US011077061B2

(12) United States Patent
Vaughn et al.

(10) Patent No.: US 11,077,061 B2
(45) Date of Patent: *Aug. 3, 2021

(54) ORAL RAPAMYCIN NANOPARTICLE PREPARATIONS AND USE

(71) Applicant: Rapamycin Holdings, Inc., San Antonio, TX (US)

(72) Inventors: Dana Vaughn, Seguin, TX (US); Neal K. Vail, Castle Hills, TX (US)

(73) Assignee: Rapamycin Holdings, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/527,398

(22) Filed: Jul. 31, 2019

(65) Prior Publication Data

US 2019/0350856 A1 Nov. 21, 2019

Related U.S. Application Data

(63) Continuation of application No. 15/109,278, filed as application No. PCT/US2014/073097 on Dec. 31, 2014, now Pat. No. 10,391,059.

(60) Provisional application No. 62/040,000, filed on Aug. 21, 2014, provisional application No. 61/980,095, filed on Apr. 16, 2014, provisional application No. 61/922,800, filed on Dec. 31, 2013.

(51) Int. Cl.
| *A61K 31/436* | (2006.01) |
| *A61K 9/16* | (2006.01) |
| *A61K 9/51* | (2006.01) |
| *A61K 9/14* | (2006.01) |
| *A61K 9/00* | (2006.01) |

(52) U.S. Cl.
CPC ............ *A61K 9/146* (2013.01); *A61K 9/0053* (2013.01); *A61K 9/141* (2013.01); *A61K 31/436* (2013.01)

(58) Field of Classification Search
CPC ........... A61K 31/436; A61K 9/16; A61K 9/51
See application file for complete search history.

(56) References Cited

U.S. PATENT DOCUMENTS

| 3,929,992 A | 12/1975 | Sehgal et al. |
| 3,993,749 A | 11/1976 | Seghal et al. |
| 4,316,885 A | 2/1982 | Rakhit |
| 4,401,653 A | 8/1983 | Eng |
| 4,460,722 A | 7/1984 | Igarashi et al. |
| 4,885,171 A | 12/1989 | Surendra et al. |
| 5,023,262 A | 6/1991 | Caufield et al. |
| 5,023,263 A | 6/1991 | Von Burg |
| 5,023,264 A | 6/1991 | Caufield et al. |
| 5,066,493 A | 11/1991 | Sehgal et al. |
| 5,078,999 A | 1/1992 | Warner et al. |
| 5,080,899 A | 1/1992 | Sturm et al. |
| 5,100,883 A | 3/1992 | Schiehser |
| 5,100,899 A | 3/1992 | Calne |
| 5,102,876 A | 4/1992 | Caufield |
| 5,118,677 A | 6/1992 | Caufield |
| 5,118,678 A | 6/1992 | Kao et al. |
| 5,120,725 A | 6/1992 | Kao et al. |
| 5,120,726 A | 6/1992 | Failli et al. |
| 5,120,727 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,151,413 A | 9/1992 | Caufield et al. |
| 5,162,333 A | 11/1992 | Failli et al. |
| 5,164,399 A | 11/1992 | Failli et al. |
| 5,169,851 A | 12/1992 | Hughes et al. |
| 5,177,203 A | 1/1993 | Failli et al. |
| 5,194,447 A | 3/1993 | Kao |
| 5,202,332 A | 4/1993 | Hughes et al. |
| 5,206,018 A | 4/1993 | Sehgal et al. |
| 5,221,670 A | 6/1993 | Caufield |
| 5,221,740 A | 6/1993 | Hughes |
| 5,233,036 A | 8/1993 | Hughes |
| 5,260,299 A | 11/1993 | Failli et al. |
| 5,260,300 A | 11/1993 | Hu |
| 5,262,423 A | 11/1993 | Kao |
| 5,262,424 A | 11/1993 | Kao |
| 5,286,731 A | 2/1994 | Caufield et al. |
| 5,288,711 A | 2/1994 | Mitchell et al. |

(Continued)

FOREIGN PATENT DOCUMENTS

| CA | 2572100 A1 | 6/2007 |
| CN | 1863509 | 11/2006 |

(Continued)

OTHER PUBLICATIONS

Amornphimoltham, P et al: "A retroninhibition approach reveals a tumor cell-autonomous response to rapamycin in head and neck cancer", Cancer Research vol. 68, No. 4, Feb. 2008, pp. 1144-1153.
Amornphimoltham, P et al: Mammalian target of rapamycin, a molecular target in squamous cell carcinomas of the head and neck; Cancer Research, vol. 65, No. 21, Nov. 2005, pp. 9953-9961.
Austad, Steven N., "Mixed results for dieting monkeys", News & Views, Nature, 2012 Macmillan Publishers Limited; dol:10.1038/nature11484.
Bove, J et al: Fighting neurodegeneration with rapamycin: mechanistic insights; Nature Review, Neuroscience, Nature Publishing Group, GB; vol. 12, No. 8, Aug. 1, 2011, pp. 437-452.
Caccamo, A et al, "Molecular Interplay Between Mammalian Target of Rapamycin (mTOR), Amyloid-β, and Tau", Journal of Biological Chemistry, Apr. 23, 2010, vol. 285, No. 17, p. 13107-13121.

(Continued)

*Primary Examiner* — Zohreh A Fay
(74) *Attorney, Agent, or Firm* — William H. Quirk; Jesse L. Frizzell; Rosenthal Pauerstein Sandoloski Agather, LLP

(57) ABSTRACT

Oral preparations of microcapsules and nanoparticles including an inhibitor of the mammalian target of rapamycin. The preparations are intended to assist with the treatment and prevention of cancer, neurocognitive dysfunction, genetically predisposed disorders, and age-related disorders. The embodiments discussed address the present need for alternative preparations or manufacturing processes that ensure efficacy while improving other performance characteristics such as storage stability, biodistribution, dosage cost, etc.

6 Claims, 4 Drawing Sheets

(56) References Cited

U.S. PATENT DOCUMENTS

| | | |
|---|---|---|
| 5,302,584 A | 4/1994 | Kao et al. |
| 5,310,903 A | 5/1994 | Goulet et al. |
| 5,321,009 A | 6/1994 | Baeder et al. |
| 5,344,833 A | 9/1994 | Hughes |
| 5,346,893 A | 9/1994 | Failli et al. |
| 5,358,944 A | 10/1994 | Caufield |
| 5,362,718 A | 11/1994 | Skotnicki et al. |
| 5,373,014 A | 12/1994 | Failli et al. |
| 5,378,696 A | 1/1995 | Caufield |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,446,048 A | 8/1995 | Faille et al. |
| 5,463,048 A | 10/1995 | Skotnicki et al. |
| 5,480,988 A | 1/1996 | Failli et al. |
| 5,480,989 A | 1/1996 | Kao et al. |
| 5,484,790 A | 1/1996 | Failli et al. |
| 5,484,791 A | 1/1996 | Failli et al. |
| 5,486,522 A | 1/1996 | Failli et al. |
| 5,486,523 A | 1/1996 | Failli et al. |
| 5,486,524 A | 1/1996 | Failli et al. |
| 5,488,054 A | 1/1996 | Failli et al. |
| 5,489,595 A | 2/1996 | Failli et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,504,204 A | 4/1996 | Failli et al. |
| 5,504,291 A | 4/1996 | Goble et al. |
| 5,508,285 A | 4/1996 | Nelson et al. |
| 5,508,286 A | 4/1996 | Skotnicki et al. |
| 5,508,290 A | 4/1996 | Nelson et al. |
| 5,508,399 A | 4/1996 | Kao et al. |
| 5,516,780 A | 5/1996 | Skotnicki et al. |
| 5,519,031 A | 5/1996 | Skotnicki et al. |
| 5,521,194 A | 5/1996 | Nelson et al. |
| 5,525,610 A | 6/1996 | Caufield et al. |
| 5,530,007 A | 6/1996 | Kao et al. |
| 5,530,121 A | 6/1996 | Kao et al. |
| 5,532,355 A | 7/1996 | Skotnicki et al. |
| 5,536,729 A | 7/1996 | Waranis et al. |
| 5,541,191 A | 7/1996 | Skotnicki et al. |
| 5,541,192 A | 7/1996 | Skotnicki et al. |
| 5,550,133 A | 8/1996 | Failli et al. |
| 5,552,160 A | 9/1996 | Liversidge et al. |
| 5,559,112 A | 9/1996 | Skotnicki et al. |
| 5,559,119 A | 9/1996 | Skotnicki et al. |
| 5,559,120 A | 9/1996 | Kao et al. |
| 5,559,121 A | 9/1996 | Harrison et al. |
| 5,559,122 A | 9/1996 | Nelson et al. |
| 5,561,138 A | 10/1996 | Armstrong |
| 5,563,145 A | 10/1996 | Failli et al. |
| 5,567,709 A | 10/1996 | Skotnicki et al. |
| 5,575,987 A | 11/1996 | Kamei et al. |
| 5,637,590 A | 6/1997 | Skotnicki et al. |
| 5,665,772 A | 9/1997 | Cottens et al. |
| 5,780,462 A | 7/1998 | Lee et al. |
| 5,891,469 A | 4/1999 | Amselem |
| 5,912,253 A | 6/1999 | Cottens et al. |
| 5,922,730 A | 7/1999 | Hu et al. |
| 5,932,243 A | 8/1999 | Fricker et al. |
| 5,952,373 A | 9/1999 | Lanzendorfer et al. |
| 5,955,457 A | 9/1999 | Lee et al. |
| 5,985,890 A | 11/1999 | Cottens et al. |
| 5,989,591 A | 11/1999 | Nagi |
| 6,004,973 A | 12/1999 | Guitard et al. |
| 6,015,809 A | 1/2000 | Zhu et al. |
| 6,197,781 B1 | 3/2001 | Guitard et al. |
| 6,200,985 B1 | 3/2001 | Cottens et al. |
| 6,204,243 B1 | 3/2001 | Posanki |
| 6,228,396 B1 | 5/2001 | Watts |
| 6,329,386 B1 | 12/2001 | Mollison |
| 6,386,869 B1 | 5/2002 | Zegarelli |
| 6,399,625 B1 | 6/2002 | Zhu |
| 6,440,990 B1 | 8/2002 | Cottens et al. |
| 6,475,518 B1 | 11/2002 | Baumgart et al. |
| 6,486,099 B2 | 11/2002 | Igari et al. |
| 6,503,883 B1 | 1/2003 | Posanki |
| 6,537,195 B2 | 3/2003 | Forman |
| 6,555,132 B1 | 4/2003 | Brox et al. |
| 6,569,463 B2 | 5/2003 | Patel et al. |
| 6,592,916 B2 | 7/2003 | Soeda et al. |
| 6,596,268 B1 | 7/2003 | Coffey et al. |
| 6,605,298 B1 | 8/2003 | Leigh et al. |
| 6,649,157 B2 | 11/2003 | Coffey et al. |
| 6,653,256 B1 | 11/2003 | Wolf et al. |
| 6,670,355 B2 | 12/2003 | Azrolan et al. |
| 6,677,357 B2 | 1/2004 | Zhu et al. |
| 6,680,330 B2 | 1/2004 | Zhu et al. |
| 6,849,651 B2 | 2/2005 | Danishefsky et al. |
| 6,923,988 B2 | 8/2005 | Patel et al. |
| 6,929,818 B2 | 8/2005 | Luthra et al. |
| 6,936,644 B2 | 8/2005 | Gilleo |
| 6,956,043 B2 | 10/2005 | Guitard et al. |
| 6,974,473 B2 | 12/2005 | Barclay et al. |
| 7,008,979 B2 | 3/2006 | Schottman et al. |
| 7,037,582 B2 | 5/2006 | Xing et al. |
| 7,041,046 B2 | 5/2006 | Forman |
| 7,041,283 B1 | 5/2006 | Achim et al. |
| 7,084,171 B2 | 8/2006 | Grainer et al. |
| 7,132,458 B2 | 11/2006 | Burton et al. |
| 7,160,867 B2 | 1/2007 | Abel et al. |
| 7,220,755 B2 | 5/2007 | Betts et al. |
| 7,241,771 B2 | 7/2007 | Zhu |
| 7,268,144 B2 | 9/2007 | Gu et al. |
| 7,271,177 B2 | 9/2007 | Benjamin et al. |
| 7,273,874 B2 | 9/2007 | Graziani et al. |
| 7,279,562 B2 | 10/2007 | Molnar-Kimber |
| 7,282,505 B2 | 10/2007 | Zhu et al. |
| 7,292,885 B2 | 11/2007 | Scott et al. |
| 7,304,033 B2 | 12/2007 | Larsen et al. |
| 7,445,916 B2 | 11/2008 | Gu et al. |
| 7,446,111 B2 | 11/2008 | Benjamin et al. |
| 7,452,723 B2 | 11/2008 | Coffey et al. |
| 7,455,853 B2 | 11/2008 | Mollison et al. |
| 7,470,682 B2 | 12/2008 | Graziani et al. |
| 7,476,678 B2 | 1/2009 | Graziani et al. |
| 7,488,444 B2 | 2/2009 | Furst et al. |
| 7,511,070 B2 | 3/2009 | Grainger et al. |
| 7,517,342 B2 | 4/2009 | Scott et al. |
| 7,517,362 B2 | 4/2009 | Shanley et al. |
| 7,519,418 B2 | 4/2009 | Scott et al. |
| 7,538,119 B2 | 5/2009 | Gu et al. |
| 7,541,380 B2 | 6/2009 | Bianchi et al. |
| 7,560,457 B2 | 7/2009 | Graziani et al. |
| 7,576,903 B2 | 8/2009 | Yamamoto et al. |
| 7,763,271 B1 | 7/2010 | Ding |
| 8,007,831 B2 | 8/2011 | Lewis et al. |
| 8,053,444 B2 | 11/2011 | Revin et al. |
| 8,383,671 B1 | 2/2013 | Consigny |
| 8,911,786 B2 | 12/2014 | Desai et al. |
| 2001/0026807 A1 | 4/2001 | Watts |
| 2002/0009473 A1 | 1/2002 | Tebbe |
| 2002/0012680 A1 | 1/2002 | Patel et al. |
| 2003/0215496 A1 | 11/2003 | Patel et al. |
| 2004/0010002 A1 | 1/2004 | Wasik et al. |
| 2004/0074089 A1 | 4/2004 | Gilleo |
| 2004/0121155 A1 | 6/2004 | Matsunami et al. |
| 2005/0032825 A1 | 2/2005 | Metcalf et al. |
| 2005/0090553 A1 | 4/2005 | Shapiro |
| 2005/0113282 A1 | 5/2005 | Parekh et al. |
| 2006/0040910 A1 | 2/2006 | Pulley et al. |
| 2006/0115533 A1 | 6/2006 | Guitard et al. |
| 2006/0121122 A1 | 6/2006 | Nakajima et al. |
| 2006/0182771 A1 | 8/2006 | Dor et al. |
| 2006/0210638 A1 | 9/2006 | Liversidge et al. |
| 2006/0234053 A1 | 10/2006 | Yamamoto et al. |
| 2006/0251710 A1 | 11/2006 | Kwon et al. |
| 2006/0251720 A1 | 11/2006 | Penhasi et al. |
| 2006/0264453 A1 | 11/2006 | Mudumba et al. |

(56) References Cited

U.S. PATENT DOCUMENTS

| | | |
|---|---|---|
| 2007/0082829 A1 | 4/2007 | Smets et al. |
| 2007/0104783 A1 | 5/2007 | Domb et al. |
| 2007/0138673 A1 | 6/2007 | Lee et al. |
| 2007/0142423 A1 | 6/2007 | Graziani et al. |
| 2007/0185150 A1 | 8/2007 | Bedrosian |
| 2007/0203168 A1 | 8/2007 | Zhao |
| 2007/0203170 A1 | 8/2007 | Zhao |
| 2007/0203171 A1 | 8/2007 | Zhao |
| 2007/0203172 A1 | 8/2007 | Zhao |
| 2007/0225313 A1 | 9/2007 | Zhao |
| 2007/0280992 A1 | 12/2007 | Margaron et al. |
| 2008/0022965 A1 | 1/2008 | Bysreen et al. |
| 2008/0069797 A1 | 3/2008 | Roncarolo et al. |
| 2008/0085880 A1 | 4/2008 | Viswanath et al. |
| 2008/0091008 A1 | 4/2008 | Viswanath et al. |
| 2008/0107749 A1 | 5/2008 | Maitra et al. |
| 2008/0138405 A1 | 6/2008 | Raheja et al. |
| 2008/0182867 A9 | 7/2008 | Wasik et al. |
| 2008/0188511 A1 | 8/2008 | Beckmann et al. |
| 2008/0193653 A1 | 8/2008 | Oh |
| 2008/0234380 A1 | 9/2008 | Shapiro |
| 2008/0249123 A1 | 10/2008 | Gu et al. |
| 2008/0255029 A1 | 10/2008 | Marks et al. |
| 2008/0275076 A1 | 11/2008 | Holm et al. |
| 2009/0186923 A1 | 7/2009 | Armer et al. |
| 2009/0324671 A1 | 12/2009 | Ngo et al. |
| 2010/0105637 A1 | 4/2010 | Kim |
| 2010/0150864 A1 | 6/2010 | Hickman et al. |
| 2010/0303901 A1 | 12/2010 | Shimoni et al. |
| 2011/0020312 A1 | 1/2011 | Narain et al. |
| 2011/0104256 A1 | 5/2011 | Wang et al. |
| 2011/0105387 A1 | 5/2011 | Wu et al. |
| 2011/0195966 A1 | 8/2011 | Garcia-Echeverria et al. |
| 2011/0200556 A1 | 8/2011 | Gutkind et al. |
| 2011/0293731 A1 | 12/2011 | Lewis et al. |
| 2012/0064143 A1 | 3/2012 | Sharp et al. |
| 2012/0276169 A1 | 11/2012 | Kang et al. |
| 2013/0035343 A1 | 2/2013 | Porta et al. |
| 2013/0039951 A1 | 2/2013 | Kim et al. |
| 2015/0202164 A1 | 7/2015 | Vail et al. |

FOREIGN PATENT DOCUMENTS

| | | |
|---|---|---|
| CN | 101361703 B | 11/2010 |
| WO | WO 1995/031194 | 11/1995 |
| WO | 2001097809 A2 | 12/2001 |
| WO | 2004004644 A2 | 1/2004 |
| WO | 2005016321 A1 | 2/2005 |
| WO | 2005034916 A1 | 4/2005 |
| WO | WO 2006/066063 | 6/2006 |
| WO | 2006072940 A2 | 7/2006 |
| WO | 2006094507 A1 | 9/2006 |
| WO | WO 2007/093346 | 8/2007 |
| WO | 2008022256 A2 | 2/2008 |
| WO | 2008027013 A2 | 3/2008 |
| WO | 2008098634 A1 | 8/2008 |
| WO | WO 2010/009335 | 1/2010 |
| WO | 2010056754 A2 | 5/2010 |
| WO | WO 2010/144846 | 12/2010 |

OTHER PUBLICATIONS

Cai, Z et al: Mammalian target of rapamycin: a valid therapeutic target through the autophagy pathway for Alzheimer's disease?; Journal of Neuroscience Research, vol. 90, No. 6, Jun. 16, 2012, pp. 1105-1118.

Chauhan, A et al: Rapamycin protects against middle cerebral artery occlusion induced focal cerebral ischemia in rats; Behavioural Brain Research, Elsevier, vol. 225, No. 2, Aug. 24, 2011, pp. 603-609.

Czerninski, R et al: A novel sustained-release clotrimazole varnish for local treatment of oral candidiasis; Clinical Oral Investigations, vol. 14, No. 1, Apr. 29, 2009, pp. 71-78.

Czerninski, R et al: Targeting mammalian target of rapamycin by rapamycin prevents tumor progression in an oral-specific chemical carcinogenesis model; Cancer Prevention Research, vol. 2, No. 1, Jan. 1, 2009, pp. 27-36.

Demetrius, Lloyd, "Aging in Mouse and Human Systems a Comparative Study", Department of Organismic and Evolutionary Biology, Harvard University, Cambridge, Massachusetts 02138, https://www.researchgate.net/c/o3og7o/iavascript/lib/pdfjs/web/viewer.html?file=https%3A.

Dufour, M et al, "Targeting the Mammalian Target of Rapamycin (mTOR) in Cancer therapy: Lessor from Past and Future Perspectives", Cancers 2011, 3 2478-2500.

Galvan, V et al; "TOR and NO as Regulators of Brain Vascular Function in a Mouse Model of AD", Oral Sessions: 02-12; Molecular and Cell Biology: APP, Abeta II, p. 191-192.

Halloran, J et al: Chronic inhibition of mammalian target of rapamycin by rapamycin components of behavior throughout lifespan in mice; Neuroscience, vol. 223, Jun. 28, 2012; pp. 102-113.

Inoki, K et al, "TSC2 Integrates Wnt and Energy Signals via a Coordinated Phosphorylation by AMPK and GSK3 to Regulate Cell Growth", Cell, Sep. 8, 2006, vol. 126, pp. 955-966.

Lin, A: Chronic rapamycin restores brain vascular integrity and function through no synthase activation and improves memory in symptomatic mice modeling Alzheimer's disease; Journal of Cerebral Blood Flow & Metabolism, vol. 33, No. 9, Sep. 1, 2013, pp. 1412-1421.

Majumder, S et al, "Inducing Autophagy by Rapamycin Before, but Not After, the Formation of Plaques and Tangles Ameliorates Cognitive Deficits", PLos One, Sep. 2011, vol. 6, Issue 9, Emory University, US.

Missiaglia, E et al, "Pancreatic EndocrineTumors: Expression Profiling Evidences a Role for AKT-mTOR Pathway", Journal of Clinical Oncology, vol. 28, No. 2, Jan. 10, 2010.

Nathan, C et al: Mammalian target of rapamycin inhibitors as possible adjuvant therapy for microscopic residual disease in head and neck squamous cell cancer; Cancer Research, vol. 67, No. 5, Mar. 2007, pp. 2160-2168.

Pignataro, G: Neuroprotective, immunosuppressant and antineoplastic properties of mTOR inhibitors: current and emerging therapeutic options; Current Opinion in Pharmacology, vol. 11, No. 4, Jun. 7, 2011, pp. 378-394.

Raimondi, AR et al: Rapamycin prevents early onset of tumorigenesis in an oral-specific K-ras and p53 two-hit carcinogenesis model, Cancer Research, American Association for Cancer Research, vol. 69, No. 10, May 1, 2009, pp. 4159-4166.

Ravikumar, B et al, "Rapamycin Pre-Treatment Protects Against Apoptosis", Human Molecular Genetics, vol. 15, No. 7,p. 1209-1216, Apr. 2006, Oxford University Press, Surrey, United Kingdom.

Spilman, P et al, "Inhibition of MTOR by Rapamycin Abolishes Cognitive Deficits and Reduces Amyloid-β Levels in a Mouse Model of Alzheimer's Disease", Apr. 2010, vol. 5, Issue 4, PLoS One vol. 5(4): p. e9979.

Wenjun, Y et al: Small molecule autophagy inducers: a new therapeutic paradigm for neural degeneration diseases; Progress in Chemistry, vol. 19, No. 12. English abstract.

Wislez, M et al, "Inhibition of Mammalian Target of Rapamycin Reverses Alveolar Epithelial Neoplasia Induced by Oncongenic K-ras", Cancer Research Apr. 15, 2005 65; 3226.

Sankhala, et al., "Review: desmoplastic small round cell tumor: current treatment approach and role of targeted therapy." Clin. Adv. Hematol. Concol., vol. 7, No. 2009, pp. 476-478.

Schwecke et al., "The biosynthetic gene cluster for the polyketide immunosuppressant rapamycin," Proc. Natl. Acad. Sci., USA, 92(17):7839-43, 1995.

Search Report issued in European Application No. 09826677.8, dated May 22, 2012.

Serruys, et al., "Rapamycin eluting stent: the onset of a new era in interventional cardiology," Heart. 87:305-307, 2002.

Shavelle et al., "Rating the Raters: Evaluating the Predictions from a Life Expectancy Rating Service," J. Insur. Med., 2009; 41(3): 178-90.

Shaw et al., "Ras, PI(3)K and mTOR signaling controls tumor cell growth." Nature. vol. 441, 2006, pp. 424-430.

(56) References Cited

OTHER PUBLICATIONS

Soerjomataram et al., "Most colorectal cancer survivors live a large proportion of their remaining life in good health," Cancer Causes Control, 2012; 23(9): 1421-1428.
Solomon, et al., "Cardiovascular Risk Associated with Celcoxib in a Clinical Trial for Colorectal Adenoma Prevention," New England J. Med. 352(11):1071-80, 2005.
Sonenberg & Hinnebusch, "Regulation of Translation Initation in Euraryotes: Mechanisms and Biological Targets," Cell. 136(4):731-45, 2009.
Steinbach, et al., "The effect of Celecoxib, a cyclooxygenase-2 inhibitor, in familial adenomatous polyposis," New England J. Med. 342(26):1946-52, 2000.
Storer, "Longevity and gross pathology at death in 22 inbred mouse strains." J. Gerontol. vol. 21, No. 3, 1966, pp. 404-409.
Supplementary Search Report in European Application No. 14772920.6 dated Aug. 1, 2016.
Tabernero et al., "Dose- and Schedule-Dependent Inhibition of the Mammalian Target of Rapamycin Pathway with Everolimus: A Phase I Tumor Pharmacodynamic Study in Patients with Advanced Solid Tumors," J. of Clinical Oncology, 2008; 26(10).
Tsang et al., "Targeting mammalian target of rapamycin (mTOR) for health and diseases," Drug Discovery Today, 12(3/4):112-124, 2007.
Ulrich, et al., "Skin Cancer in Organ Transplant Recipients—Where Do We Stand Today?", Am. J. Transplant. 8:2192-8, 2008.
Vasen, et al., Guidelines for the clinical management of familial adenomatous polyposis (FAP) Gut. vol. 57, No. 5, 2008, pp. 704-713.
Wallace et al., "Upper gastrointestinal disease in patients with familial adenomatous polyposis" Br. J. Surg. vol. 85, No. 6, 1998, pp. 742-750.
Wijnhoven, et al., "Accelerated aging pathology in ad libitum fed Xpd(TTD) mice is accompanied by features suggestive of caloric restriction." DNA Repair (Amst.) vol. 4, No. 11, 2005, pp. 1314-1324.
Yang Wenjun & Wen Longping, "Small Molecule Autophagy Induces," Progress in Chemistry, 2007; 19(12): 2013-6.
Yu, et al., "A Retrospective Study of Conversion From Tacrolimus-based to Sirolimus-based Immunosuppression in Orthotopic Liver Transplant Recipients," Exp. Clin. Transplant. 6:113-7, 2008.
Zell, et al., "Risk of Cardiovascular Events in a Randomized Placebo-Controlled, Double-Blind Trial of Difluoromethylomithine Plus Sulindac for the Prevention of Sporadic Colorectal Adenomas," Cancer Prev. Res. 2(3):209-12, 2009.
Zoncu, et al., "mTOR: from growth signal integration to cancer, diabetes and ageing," Nat. Rev. Mol. Cell Biol. 12:21-35, 2010.
Anastas et al., "WNT signalling pathways as therapeutic targets in cancer." Nat Rev Cancer. vol. 13, No. 1, 2013, pp. 11-26.
Blagosklonny, "Aging and immortality: quasi-programmed senescence and its pharmacologic inhibition," Cell Cycle, 5(18):2087-102, 2006.
Blagosklonny, An anti-aging drug today: from senescence-promoting genes to anti-aging pill, Drug Discov Today, 12(5-6):218-24, 2007.
Boulanger, et al., "Human Herpesvirus-8 (HHV-8)-Associated Primary Effusion Lymphoma in Two Renal Transplant Recipients Receiving Rapamycin," Am J. Transplant. 8:707-10, 2008.
Bulow, et al., "Duodenal adenomatosis in familial adenomatous polyposis," Gut. 53(3): 381-6, 2004.
Campistol, "Minimizing the risk of posttransplant malignancy." Transplantation Proceedings, vol. 40, No. 10, Supplement, S40-S43, 2008.
Cao et al., "Toll-like receptor-mediated induction of type I interferon in plasmacytoid dendritic cells requires the rapamycin-sensitive PI(3)K-mTOR-p70S6K pathway," Nat Immmunol. Oct. 2008; 9(10):1157-64.
Carter et al., "Molecular mechanisms of life-and health-span extension: role of calorie restriction and exercise intervention," Appl. Physiol Nutr Metab. 32(5):954-66, 2007.

Chauvin, et al., "Ribosomal protein S6 kinase activity controls the ribosome biogenesis transcriptional program." Oncogene. vol. 33, 2014, pp. 474-483.
Cheung, et al., "Complete deletion of Apc results in severe polyposis in mice," Oncogene, 29:1857-64, 2010.
Cruzado et al., "Nonimmunosuppressive effects of mammalian target of rapamycin inhibitors," Transplantation Reviews, 2007; 21(1): 73-81.
Efeyan & Sabatini, "mTOR and cancer: many loops in one pathway," Curr Opin Cell Biol. 22(2): 169-76, 2009.
Estep et al., "Short-term calorie restriction in male mice feminizes gene expression and alters key regulators of conserved aging regulatory pathways," PLoS One. 2009;4(4):e5242.
Fajadet et al., "Randomized, double-blind, multicenter study of the Endeavor zotarolimus-eluting phosphorylcholine-encapsulated stent for treatment of native coronary artery lesions. Clinical and angiographic results of the ENDEAVOR II Trial" Minerva Cardioangiol. Feb. 2007; 55(1):1-18.
Finkel, et al., "The common biology of cancer and ageing." Nature, 448:767-774, 2007.
Fujishita, et al., "Inhibition of the mTORC1 pathway suppresses intestinal polyp formation and reduces mortality in Apc/\716 mice," Proc Nat'l Acad Sci USA. 105(36):13544-9, 2008.
Ghanbarzadeh, et al., "Improvement of the antiproliferative effect of rapamychin on tumor cell lines by poly (monomethylitaconate)-based pH-sensitive, plasma stable liposomes." Colloids and Surface. 115:323-30, 2014.
Giardiello, et al., "Treatment of colonic and rectal adenomas with sulindac in familial adenomatous polyposis," New England J. Med. 328(18):1313-6, 1993.
Graziani, et al. "Recent advances in the chemistry, biosynthesis and pharmacology of rapamycin analogs." Nat Prod Rep. vol. 26, No. 5, 2009, pp. 602-609.
Gregory et al., "Isolation and characterization of pre-rapamycin, the first macrocyclic intermediate in the biosynthesis of the immunosuppressant rapamycin by S. hygroscopicus." Angew Chem Int Ed Engl. Bol. 43, No. 19, 2004, pp. 2551-2553.
Gregory et al., "Rapamycin biosynthesis: Elucidation of gene product function." Org Biomol Chem. vol. 4, No. 19, 2006, pp. 3565-3568.
Guertin and Sabatini, "The pharmacology of mTOR inhibition." Sci. Signal., 2(67):pe24, 2009.
Hansen et al., "Lifespan extension by conditions that inhibit translation in Caenorhabditis elegans," Aging Cell, 6:95-110, 2007.
Harrison, et al., "Rapamycin fed late in life extends lifespan in genetically heterogeneous mice," Nature. 460(7253):392-5, 2009.
Hasty, et al., "eRapa Restores a Normal Life Span in a FAP Mouse Model." Cancer Prev. Res. 7:169-178, 2014.
Hursting, et al., "Calorie restriction, aging, and cancer prevention; mechanisms of action and applicability to humans." Annu Rev. Med., vol. 54, 2003, pp. 131-152.
International Preliminary Report on Patentability issued on PCT/US2014/026329, dated Sep. 24, 2015.
International Search Report and Written Opinion issued in PCT/US14/26329, dated Jul. 3, 2014.
Janus, et al., "The mammalian target of the rapamycin (mTOR) kinase pathway; its role in tumourigenesis and targeted antiturnor therapy," Cell Mol. Biol. Lett. 10(3):479-98, 2005.
Jhunjhunwala, et al., "Delivery of Rapamycin to Dendritic Cells Using Degradable Microparticles," J Control Release. 133:191-197, 2009.
Kapahi et al., "Regulation of lifespan in *Drosophila* by modulation of genes in the TOR signaling pathway," Curr. Biol., 14:885-890, 2004.
Kim, et al., "Chemoprevention in familial adenomatous polyposis." Best Pract. Res. Clin. Gastroenterol. 25(4-5):607-22, 2011.
Kinzler, et al., "Identification of FAP locus genes from chromosome 5q21." Science. vol. 253, No. 5020, 1991, pp. 661-665.
Koehl, et al., "Rapamycin inhibits oncogenic intestinal ion channels and neoplasia in APC/\min/+mice," Oncogene, 29:1553-60, 2010.
Korinek, et al., "Constitutive transcriptional activation by a beta-catenin-Tcf complex in APC-/- colon carcinoma." Science. vol. 275, 1997, pp. 1784-1787.

(56) References Cited

OTHER PUBLICATIONS

Kunstyr, et al., "Gerontological data of C57BL/6J mice. I. Sex differences in survival curves." J Gerontol. vol. 30, Nos. 2, 1975, pp. 157-162.

Labayle, et al., "Sulindac causes regression of rectal polyps in familial adenomatous polyposis." Gastroenterology. vol. 101, No. 3, 1991, pp. 635-639.

Leung et al., "Challenging the 10-year rule: The accuracy of patient life expectancy predictions by physicians in relation to prostate cancer management." Can. Urol. Assoc. J., 2012; 6(5): 367-73.

Masoro, "Overview of caloric restriction and ageing." Mech. Ageing Dev. vol. 126, 2005, pp. 913-922.

Miller et al., "An aging interventions testing program: study design and interim report," Aging Cell, 6:565-575, 2007.

Miller, et al., "Multimodal imaging of growth and rapamycin-induced regression of colonic adenomas in Apc mutation-dependent mouse," Translational Oncol. 5(5):313-20, 2012.

Miller, et al., "Rapamycin, But Not Resveratrol or Simvastatin, Extends Life Span of Genetically Heterogeneous Mice," J Gerontol. A. Biol. Sci. Med. Sci. 66(2):191-201, 2011.

Morin, et al., "Activation of beta-catenin-Tcf signaling in colon cancer by mutations in beta-catenin or APC." Science. vol. 275, 1997, pp. 1787-1790.

Nadon et al., "Design of aging intervention studies: the NIA interventions testing program," AGE, 30(4):187-199, 2008.

Pallet, et al., "Sirolimus early graft nephrotoxicity; clinical and experimental data" Curr. Drug Saf. vol. 1, 2006, pp. 179-187.

PCT International Preliminary Report on Patentability issued in international Application No. PCT/US2009/064044, dated May 26, 2011.

PCT International Search Report and Written Opinion issued in international application No. PCT/US2009/064044, dated Jun. 25, 2010.

Powers III et al., "Extension of chronological life span in yeast by decreased TOR pathway signaling," Genes & Development, 20:174-184, 2006.

Rao et al., "Mammalian Target of Rapamycin (mTOR) Inhibitors as Anti-Cancer Agents," Current Cancer Drug Targets, 2004; 4(8):621-635.

Rigau, et al., "Effects of long-term sulindac therpay on colonic polyposis," Ann. Int. Med., vol. 115, No. 12, 1991, pp. 952-954.

ORAL RAPAMYCIN NANOPARTICLE PREPARATIONS AND USE

CROSS-REFERENCE TO RELATED APPLICATION

This application relates to the subject matter of U.S. patent application Ser. No. 13/128,800, filed Nov. 11, 2009, published under Publication No. 2012/0064143, entitled "Inhibition of Mammalian Target of Rapamycin," which has original priority dating to Nov. 11, 2008 (for reference, the "Related UT Application"). Subject matter disclosed or claimed in this patent application has been developed in cooperation with representatives of the Board of Regents of the University of Texas System, which is assignee of record for the Related UT Application.

CLAIM OF PRIORITY TO PRIOR APPLICATION

This application is a continuation of prior filed co-pending U.S. Non-Provisional patent application Ser. No. 15/109,278, filed on Jun. 30, 2016, entitled "Oral Rapamycin Nanoparticle Preparations and Use", which is a U.S. National Stage Application of International Patent Application Serial No. PCT/US2014/073097, filed on Dec. 31, 2014, entitled "Oral Rapamycin Nanoparticle Preparations and Use", which claims the benefit of the filing date of U.S. Provisional Application Ser. No. 62/040,000 filed on 21 Aug. 2014, entitled "Oral Rapamycin Nanoparticle Preparations and Use in the Treatment of Hemolytic Anemia in Dogs"; Ser. No. 61/980,095 filed on 16 Apr. 2014, entitled "Oral Rapamycin Nanoparticle Preparations and Use in the Treatment of Inflammatory Gum Disease in Cats"; and Ser. No. 61/922,800, filed on 31 Dec. 2013, entitled "Oral Rapamycin Nanoparticle Preparations", the entire disclosures of which are hereby incorporated by reference into the present disclosure.

STATEMENT REGARDING FEDERALLY SPONSORED RESEARCH

Not applicable for this patent application, although certain rights in the subject matter of the Related UT Application may be owned by the United States government.

BACKGROUND

1. Field of the Invention

The present invention relates generally to manufacture and use of mTOR inhibitors for oral administration in the prevention and treatment of medical maladies in humans and other animals. More particularly, the invention relates to manufacture and use of preparations for oral administration that include an mTOR and/or mTOR complex 1 (mTORC1) inhibitor together with protective polymers and stabilizers, for prevention and treatment of medical maladies, most especially in the fields of oncology, neurology and autoimmunities, as well as healthy lifespan extension in humans and other animals.

2. Description of Related Art

Rapamycin (also known as sirolimus) is a well-known pharmaceutical agent that has long been used to minimize organ transplant rejection. Rapamycin and its numerous analogs and derivatives (collectively known as "rapalogs") famously act to inhibit its namesake metabolic pathway in mammals—the mammalian target of rapamycin ("mTOR"). The critical metabolic roles of the mTOR pathway have long led to broad speculation about possible medical uses for rapamycin outside of organ transplant rejection. However, despite the success with prevention of transplant rejection, and despite the many long-felt needs and corresponding tremendous efforts in developing rapamycins for other indications, effective use of rapamycin for treating or preventing other disorders has not been widely successful and has been very limited at best. The reader should refer to the Related UT Application, which has been incorporated by reference, for additional technical descriptions and a detailed description of the related art.

Particular formulations taught in the Related UT Application (the "2008 Discoveries") provided particles or "cores" containing the active rapamycin ingredient, and those cores were microencapsulated within a protective polymer matrix, for oral administration of the rapamycin. The rapamycin cores were preferably microencapsulated using a spinning disk atomization coating process with a protective polymer matrix known under the "EUDRAGIT® S 100" name. The EUDRAGIT® S 100 polymer matrix principally consists of a particular methacrylate polymer that is generally stable at pH levels below 7 and was used to protect the rapamycin from degrading in the acidic conditions of the stomach. Then, once the microencapsulated rapamycin entered basic conditions (i.e., pH greater than 7) within the intestines, the protective matrix would dissolve and, theoretically, the undegraded rapamycin would be absorbed through the intestinal walls and become bioavailable for its intended medical purposes.

Unfortunately, theory and practice do not always match perfectly. Despite tremendous hope for broad efficacy of the orally administered use of such microencapsulated rapamycin preparations, and despite widespread national and international attention to the 2008 Discoveries, significant concerns remained about whether effective levels of rapamycin could be reliably delivered to the body in this form. For reasons that long remained uncertain in practice, stability of the basic rapamycin molecule within such formulations has been less reliable than desired, and uncertainties have mounted with respect to whether enteric absorption levels can be reliable enough for adequate market acceptance of the 2008 Discoveries.

Other challenges exist. It is counterintuitive to even consider the use of rapamycin and other mTOR inhibitors for prevention or treatment of conditions such as feline gingivitis or canine hemolytic anemia. Particularly because one of the contraindications or precautions commonly associated with rapamycin relates to mouth ulcers. For a variety of reasons, rapamycin tends to cause mucous membrane breakdown in oral cavities in some subjects, particularly in certain doses. That alone would sufficiently deter someone from using rapamycin for these applications.

Consequently, there is a need for improved encapsulated rapamycin preparations—preparations that still capitalize on the 2008 discoveries but that improve various performance characteristics, such as storage stability, biodistribution, dosage cost, etc.

In addition, because the potential applications are so wide and varied and yet relatively unproven for an oral form of rapamycin, that wide variety itself presents an impediment to realizing publically available use of such a preparation. Given the market dynamics and regulatory requirements of pharmaceutical industries, a successful effort to actually make embodiments of the 2008 Discoveries available for use by the public would require much more than minimizing uncertainties about the preparation itself. A successful effort to do so must identify and validate a particular, highly-impactful indication for which the benefits of using a microencapsulated rapamycin would be relatively irrefutable, and the effort must likewise develop corresponding methods and strategies for effectively and reliably addressing as much.

SUMMARY OF THE INVENTION

While the present invention is multifaceted, it can be embodied in numerous improved forms of encapsulated rapamycins and in methods for reliably producing and using these improved forms. The improved forms of encapsulated rapamycins preferably provide nanoparticles containing mTOR inhibitors within a protective polymer matrix for oral administration of rapamycin. The result is not only more durable and stable, but is also more bioavailable and efficacious for treatment and prevention of medical maladies, particularly of genetically-predisposed disorders and age-related disorders, especially in the fields of oncology, neurology and auto-immune disorders in humans and other animals.

The various embodiments improve on the related art, including by optimizing stability, manufacturability, bioabsorption, biodistribution, dosage cost, efficacy and the like. Although the embodiments addressed below do not compose an exhaustive list, this specification describes embodiments comprising controlled release encapsulated rapamycin; rapamycin nanoparticle inclusions; rapamycin nanoparticle morphology; free radical scavengers and oxidative stabilizers; and an albumin-rapamycin nanoparticle.

In the disclosed methods, the composition comprising rapamycin or an analog of rapamycin may be delivered in any suitable manner. In a preferred embodiment, the composition comprising rapamycin or an analog of rapamycin is orally administered to the subject.

Compositions comprising rapamycin or an analog of rapamycin may include a nanoparticle construct combined with a carrier material preferably an enteric composition for purposes of minimizing degradation of the composition until it passes the pylorus to the intestines of the subject. Compositions comprising rapamycin or an analog of rapamycin may also include a hydrophilic, swellable, hydrogel forming material. Such compositions may be encased in a coating that includes a water insoluble polymer and a hydrophilic water permeable agent. In some embodiments, the water insoluble polymer is a methyl methacrylate-methacrylic acid copolymer. Compositions comprising rapamycin or an analog of rapamycin may further include a thermoplastic polymer for purposes of gradual or controlled release of the rapamycin or an analog of rapamycin. Examples of the thermoplastic polymer include EUDRAGIT® Acrylic Drug Delivery Polymers (Evonik Industries AG, Germany).

In some embodiments, rapamycin particles or particles of rapamycin analogs or other mTOR inhibitors or analogs thereof, are encapsulated or coated, or the composition comprising the rapamycin or other mTOR inhibitor or analog thereof is encapsulated or coated. For reference purposes in these descriptions, "microencapsulation" (and its grammatical variations) should be interpreted to refer to protection of microparticle or nanoparticle forms of rapamycins (preferably in the nanoparticle forms according to the descriptions herein) by combining such particles with an enteric coating material or the like that is formulated to resist degradation in acidic conditions. Further, the designations "microencapsulated rapamycin" and "enteric-coated rapamycin" are used interchangeably to refer generically to each and every variation of microencapsulated rapamycins, especially to those variations that are described or particularly suggested in these descriptions, and equivalents thereof. Exceptions in particular contexts should be understood, nonetheless, to the extent that the context makes more specific or contrary clarifications for that context. In some embodiments, the encapsulant or coating used for and incorporated in enteric-coated rapamycin preparations may be an enteric coating. In another aspect of these descriptions, general references to "prevention and treatment" (or the like) of a malady should be interpreted to include reference not only to prevention and treatment of the actual malady, but also to delay or reduction in the progression of that malady as well as prevention and treatment of its precursors and sequelae.

In many embodiments involving enteric-coated rapamycin preparations, the rapamycins, rapamycin analogs, or related compositions within the enteric-coated rapamycin preparation are provided in the form of nanoparticles that include the rapamycin or other mTOR inhibitor, in which cases the designation "nanoRapa" is generically used for reference purposes in these descriptions, while the form of rapamycin used may preferably include, but not be limited to, an encapsulated form in the form of nanoparticles designated as "enteric-coated rapamycinNP2g." After preparing the nanoRapa preparations through any of various approaches that may be understood and/or described herein, the nanoRapa preparation may then be coated with an enteric coating to provide an enteric-coated rapamycin preparation formed from nanoRapa particles. For reference purposes in these descriptions, the designation "e-nanoRapa" is generically used to refer to each and every enteric-coated rapamycin variation formed from nanoRapa particles.

Many other objects, features and advantages of the present invention will become apparent to those of ordinary skill in the art, particularly after a thorough review of the public literature in the field, and all the more from the following detailed descriptions and accompanying illustrations and claims. It should be understood, however, that the detailed description and the specific examples, while indicating preferred embodiments of the invention, are given by way of illustration only, since various changes and modifications within the spirit and scope of the invention will become apparent to those skilled in the art from these detailed descriptions.

BRIEF DESCRIPTION OF THE DRAWINGS

The accompanying drawings form part of the present specification and are included to further demonstrate and illustrate certain aspects of the present invention. The invention may be better understood by reference to one or more of these drawings in combination with the detailed description of specific embodiments presented herein.

DETAILED DESCRIPTION OF PREFERRED EMBODIMENTS

Figure 1:
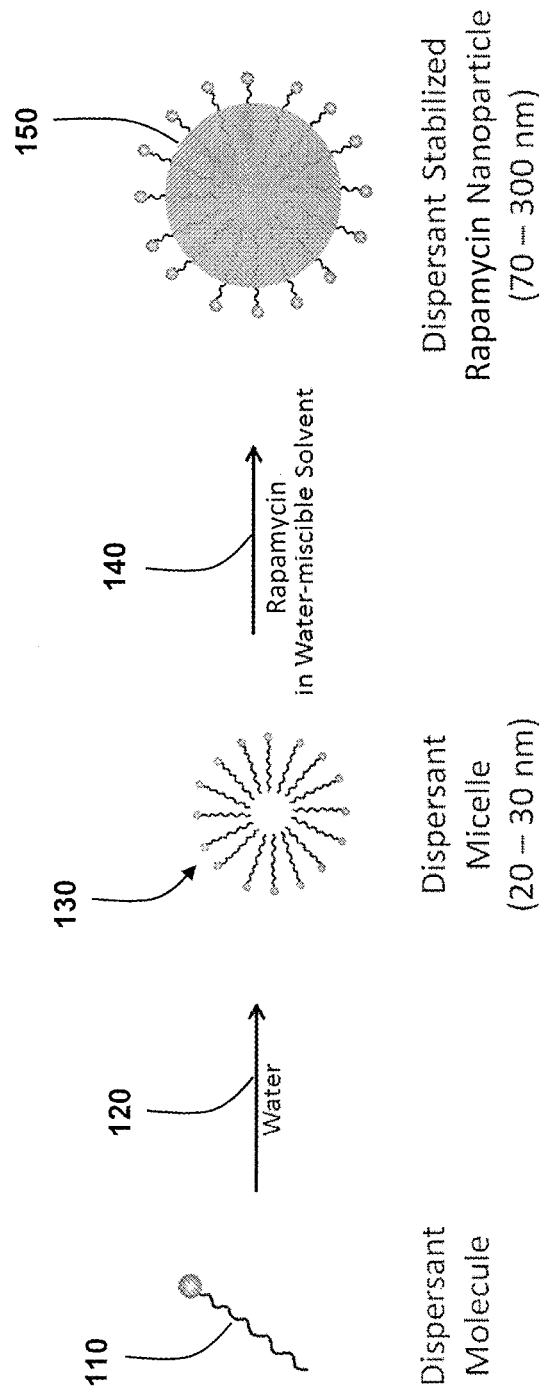
FIG. 1 is a graphic illustration of microscopic aspects of a preferred process for producing a dispersion of preferred forms of rapamycin nanoparticles according to the teachings of the present invention.

The following examples are included to demonstrate preferred embodiments of the invention. It should be appreciated by those of skill in the art that the techniques disclosed in these examples are thought to represent techniques that function well in the practice of the invention, and thus can be considered to constitute preferred modes for its practice. However, in light of the present disclosure, those of skill in the art should appreciate that many changes can be made in the specific embodiments which are disclosed while still obtaining a like or similar result without departing from the spirit and scope of the invention.

For purposes of these descriptions, a few wording simplifications should also be understood as universal, except to the extent otherwise clarified in a particular context either in the specification or in any claims. The use of the term "or" in the specification is used to mean "and/or" unless explicitly indicated to refer to alternatives only, or unless the alternatives are inherently mutually exclusive. When referencing values, the term "about" is used to indicate an approximate value, generally one that includes the standard deviation of error for any particular embodiments that are disclosed or that are commonly used for determining such value. "A" or "an" may mean one or more, unless clearly indicated otherwise. Such "one or more" meanings are most especially intended when references are made in conjunction with open-ended words such as "having," "comprising" or "including." Likewise, "another" may mean at least a second or more.

GENERAL EMBODIMENTS

Any inhibitor of mTOR is contemplated for inclusion in the present compositions and methods. In particular embodiments, the inhibitor of mTOR is rapamycin or an analog of rapamycin, preferably administered orally in the form of an enteric-coated rapamycin and/or e-nanoRapa preparation.

Rapamycin binds to a member of the FK binding protein (FKBP) family, FKBP 12. The rapamycin/FKBP 12 complex binds to the protein kinase mTOR to block the activity of signal transduction pathways. Because the mTOR signaling network includes multiple tumor suppressor genes, including PTEN, LKB1, TSC1, and TSC2, and multiple proto-oncogenes including P13K, Akt, and eEF4E, mTOR signaling plays a central role in cell survival and proliferation. Binding of the rapamycin/FKBP complex to mTOR causes arrest of the cell cycle in the G1 phase (Janus 2005).

mTORC1 inhibitors also include rapamycin analogs. Many rapamycin analogs are known in the art. Non-limiting examples of analogs of rapamycin include, but are not limited to, everolimus, tacrolimus, CC1-779, ABT-578, AP-23675, AP-23573, AP-23841, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, and 42-O-(2-hydroxy)ethyl rapamycin.

Other analogs of rapamycin include: rapamycin oximes (U.S. Pat. No. 5,446,048); rapamycin aminoesters (U.S. Pat. No. 5,130,307); rapamycin dialdehydes (U.S. Pat. No. 6,680,330); rapamycin 29-enols (U.S. Pat. No. 6,677,357); O-alkylated rapamycin derivatives (U.S. Pat. No. 6,440,990); water soluble rapamycin esters (U.S. Pat. No. 5,955,457); alkylated rapamycin derivatives (U.S. Pat. No. 5,922,730); rapamycin amidino carbamates (U.S. Pat. No. 5,637,590); biotin esters of rapamycin (U.S. Pat. No. 5,504,091); carbamates of rapamycin (U.S. Pat. No. 5,567,709); rapamycin hydroxyesters (U.S. Pat. No. 5,362,718); rapamycin 42-sulfonates and 42-(N-carbalkoxy)sulfamates (U.S. Pat. No. 5,346,893); rapamycin oxepane isomers (U.S. Pat. No. 5,344,833); imidazolidyl rapamycin derivatives (U.S. Pat. No. 5,310,903); rapamycin alkoxyesters (U.S. Pat. No. 5,233,036); rapamycin pyrazoles (U.S. Pat. No. 5,164,399); acyl derivatives of rapamycin (U.S. Pat. No. 4,316,885); reduction products of rapamycin (U.S. Pat. Nos. 5,102,876 and 5,138,051); rapamycin amide esters (U.S. Pat. No. 5,118,677); rapamycin fluorinated esters (U.S. Pat. No. 5,100,883); rapamycin acetals (U.S. Pat. No. 5,151,413); oxorapamycins (U.S. Pat. No. 6,399,625); and rapamycin silyl ethers (U.S. Pat. No. 5,120,842).

Other analogs of rapamycin include those described in U.S. Pat. Nos. 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; 5,023,262; all of which are incorporated herein by reference. Additional rapamycin analogs and derivatives can be found in the following U.S. Patent Application Pub. Nos., all of which are herein specifically incorporated by reference: 20080249123, 20080188511; 20080182867; 20080091008; 20080085880; 20080069797; 20070280992; 20070225313; 20070203172; 20070203171; 20070203170; 20070203169; 20070203168; 20070142423; 20060264453; and 20040010002.

Rapamycin or a rapamycin analog can be obtained from any source known to those of ordinary skill in the art. The source may be a commercial source or a natural source. Rapamycin or a rapamycin analog may be chemically synthesized using any technique known to those of ordinary skill in the art. Non-limiting examples of information concerning rapamycin synthesis can be found in Schwecke et al., 1995; Gregory et al., 2004; Gregory et al., 2006; Graziani, 2009.

Preferred embodiments of the present invention provide an improved form of encapsulated rapamycin—an encapsulated rapamycin nanoparticle that is more durable, stable and bioavailable, which enhances efficacy and predictability and ensures better biodistribution while also allowing improved patient compliance relative to raw rapamycin, as well as being produced at a reasonable cost. The improved form of encapsulated rapamycin preferably provides the rapamycin nanoparticles within a polymer matrix, forming an encapsulated rapamycin nanoparticle in a single drug delivery structure for oral administration of rapamycin. The polymer matrix, more particularly, is a controlled release matrix, as described elsewhere in these descriptions. This encapsulated rapamycin nanoparticle may also be referred to as an enteric-coated rapamycin nanoparticle. In addition, many of the preferred embodiments also include a stabilizing compound (for our purposes, a "stabilizer") within the controlled release matrix either to improve compatibility of the rapamycin with the controlled release matrix, to stabilize the crystalline morphology of the rapamycin, or to help further prevent degradation of the rapamycin, particularly when the encapsulated rapamycin nanoparticle is exposed to air, atmospheric moisture, or room temperature or warmer conditions. Particularly preferred embodiments incorporate the stabilizers within each rapamycin nanoparticle, although certain aspects of the invention may be embodied with stabilizers on the surface of the encapsulated rapamycin nanoparticles or otherwise dispersed in the controlled release matrix. To different levels depending on the particular approach used for producing the nanoparticles, with or without other additives, the result is more efficacious for treatment and prevention of genetically-predisposed disorders and age-related disorders, especially in the fields of oncology and neurology in humans and other animals.

Rapid anti-solvent precipitation, or controlled precipitation, is a preferred method of preparing the rapamycin nanoparticles as it provides for minimal manipulation of the rapamycin and exquisite control over nanoparticle size and distribution, and the crystallinity of the rapamycin. Several controlled precipitation methods are known in the art, including rapid solvent exchange and rapid expansion of supercritical solutions, both of which can be implemented in batch or continuous modes, are scalable, and suitable for handling pharmaceutical compounds. Preferred embodiments use an anionic approach, producing micelles 130 (illustrated in FIG. 1) or other molecular aggregations of amphipathic compounds (e.g. sodium cholate or similar surfactants with amphipathic tendencies) in concentrations greater than their critical micelle concentrations.

Figure 2:
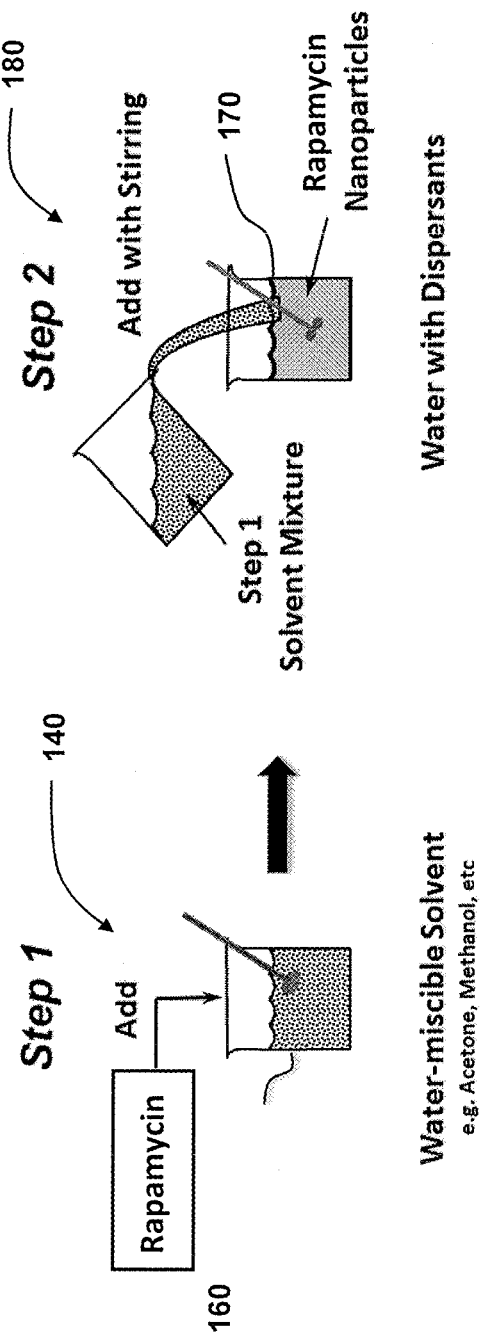
FIG. 2 is a graphic illustration of two basic steps in a preferred process for producing a dispersion of preferred forms of rapamycin nanoparticles according to the teachings of the present invention.

As part of a preferred process for producing microencapsulated rapamycin nanoparticles, FIGS. 1 & 2 illustrate basic preferred steps for producing a dispersion of preferred rapamycin nanoparticles through controlled precipitation. Rapamycin itself (sometimes referred to "raw" or "neat" rapamycin) is available in powder forms from multiple sources readily identifiable to those in the field. Although rapamycin is not readily soluble in water, solubility can be achieved in some aqueous miscible solvents.

Step 1 in FIG. 2 illustrates a first basic step in the preferred process of producing preferred rapamycin nanoparticles, whereby raw rapamycin is mixed and dissolved into an aqueous miscible solvent 160 (the mixture represented by 140 in FIG. 1). As illustrated by Step 2 in FIG. 2, the resultant solvent mixture is injected into rapidly stirred water containing an appropriate aqueous soluble dispersant, preferably sodium cholate, which is a polar amphipathic molecule that tends to form micelles from solution.

After mixing the solvent mixture with the micelle-producing aqueous dispersant in Step 2, the effects of solubility cause the rapamycin to partition to the hydrophobic micelle cores 130. Appropriate solvents 160 and dispersants 110 are discussed in greater detail below. Although the core of the micelles is relatively hydrophobic, which tends to attract the rapamycin from the solvent mixture, the results create a nanoparticle 150 having an outer surface decorated with hydrophilic ends of sodium cholate, which tend to keep the resulting nanoparticles in suspension within the final mixture.

Figure 3:
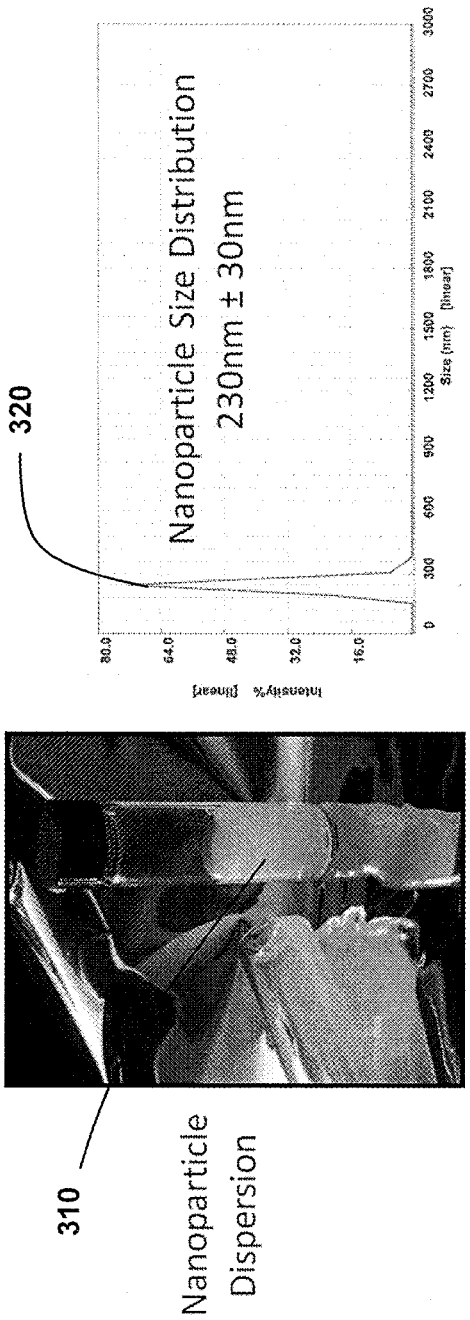
FIG. 3 provides a photograph of a dispersion of rapamycin nanoparticles produced as a result of Step 2 in the preferred process illustrated in FIG. 2, together with a graph of nanoparticle size distribution for the dispersion shown in the photograph.

A sample of a rapamycin nanoparticle dispersion 310 resulting from Step 2 is shown in the photograph in FIG. 3. FIG. 3 also shows a representative graph 320 of the resultant rapamycin nanoparticle size distribution, as indicated by the intensity of light scattered by corresponding particle sizes within the sample dispersion. The sodium cholate results in a hydrophilic surface, stabilizing the nanoparticles in the aqueous media and thereby preventing aggregation and particle growth. This product ensures enhanced and prolonged rapamycin stability—i.e., improved resistance to moisture degradation and/or oxidation for the final product—as well as good intestinal bioabsorption characteristics for the rapamycin protected in this manner.

Rapamycin nanoparticles prepared by controlled precipitation methods can be stabilized against irreversible aggregation, Ostwald ripening, and/or reduced dispersibility, by control of colloid chemistry, particle surface chemistry and particle morphology. For example, nanoparticles prepared by antisolvent solidification can be stabilized by ionic and non-ionic surfactants that adsorb to nanoparticle surfaces and promote particle colloid stability through either charge repulsion or steric hindrance, respectively. Moreover, stabilizers can affect nanoparticle crystallinity, which may be preferred to promote different biodistribution and bioavailability in certain indications.

Rapamycin nanoparticles can consist of molecular rapamycin bound by suitable methods to other nanoparticles. Suitable methods of attaching rapamycin to a nanoparticle carrier or substrate may include physical adsorption through hydrogen van der Waals forces or chemisorption through covalent or ionic bonding. Nanoparticle substrates may be either natural or synthetic, and modified to promote specific interactions with rapamycin. Natural nanoparticles include albumin and other proteins, and DNA. Synthetic nanoparticles include organic and inorganic particulates, micelles, liposomes, dendrimers, hyperbranched polymers, and other compounds.

The rapamycin nanoparticles can be processed by any suitable method, such as by milling, high pressure atomization, or rapid anti-solvent precipitation. Milling is suitable provided care is taken to minimize both rapamycin degradation and particle agglomeration. Rapamycin degradation can be reduced with the aid of cooling or cryogenic processes. Agglomeration due to the increased surface area and concomitant adhesive forces can be reduced by the use of dispersants 110 during the milling process.

The individual rapamycin nanoparticles are preferably sized in the range between about 1 nanometer and about 1 micron. Smaller sized rapamycin nanoparticles are preferred, preferably at less than 1 micron diameter, for various reasons, including better control of final particle size, improved stability within the particles, and the ability to tune bioavailability by controlling the crystallinity and composition of the rapamycin nanoparticles.

Manufacturing approaches for the encapsulated rapamycin nanoparticle drug delivery structure embodiments of the present invention include creating a solution of the controlled release matrix, with the rapamycin nanoparticles dispersed therein, in appropriate proportion and producing a heterogeneous mixture. The solvent for such mixtures can be a suitable volatile solvent for the controlled release matrix, although it is preferred the solvent be either a poor solvent or non-solvent for the rapamycin nanoparticles so that when the rapamycin nanoparticles are dispersed into the controlled release matrix solution they remain as discrete nanoparticles. The resulting dispersion of rapamycin nanoparticles in the controlled release matrix solution can then be reduced to a dry particulate powder by a suitable process, thereby resulting in microparticles of a heterogeneous nature comprised of rapamycin nanoparticles randomly distributed in the controlled release matrix. The particulate powder may also be tailored by a suitable process to achieve a preferred particle size for subsequent preparation, which may be from about 20 to about 70 microns in diameter.

The rapamycin nanoparticles are microencapsulated with the controlled release matrix using a suitable particle-forming process to form the encapsulated rapamycin nanoparticle. An example of a particle-forming process is spinning disk atomization and drying. For a detailed discussion of the apparatus and method concerning the aforementioned spin disk coating process, this application incorporates by references US Patent Applications 2011/221337 and 2011/220430, respectively. Alternatively, for example, the encapsulated rapamycin nanoparticles can be prepared by spray drying.

In some embodiments, not all of the rapamycin nanoparticles will be encapsulated within the controlled release matrix. Instead the rapamycin nanoparticles may be enmeshed with the controlled release matrix, with some of the rapamycin nanoparticles wholly contained within the controlled release matrix while another other rapamycin nanoparticles apparent on the surface of the drug delivery structure, constructed in appearance similar to a chocolate chip cookie.

Depending on the size of the rapamycin nanoparticles, the encapsulated rapamycin nanoparticles are preferably of diameter between 10 and 50 microns, although diameters as large as 75 microns may be suitable for alternatives with corresponding compromises due to the larger size.

The controlled release matrix of the encapsulated rapamycin nanoparticles can be selected to provide preferred release characteristics of the encapsulated rapamycin nanoparticles. For example, the matrix may be pH sensitive to provide either gastric release, or preferably, enteric release of the rapamycin. Enteric release of the rapamycin is preferred to achieve improved absorption and bioavailability of the rapamycin. Many materials suitable for enteric release are known in the art, including fatty acids, waxes, natural and synthetic polymers, shellac, and other materials. Polymers are a preferred enteric coating and may include copolymers of methacrylic acid and methyl methacrylate, copolymers of methyl acrylate and methacrylic acid, sodium alginate, polyvinyl acetate phthalate, and various succinate or phthalate derivatives of cellulose and hydroxypropyl methylcellulose. Synthetic polymers, such as copolymers of methacrylic acid and either methyl acrylate or methyl methacrylate, are preferred enteric release polymers due the ability to tune the dissolution pH range of these synthetic polymers by adjusting their comonomer compositions. Examples of such pH sensitive polymers are EUDRAGIT® polymers (Evonik Industries, Essen, Germany). Specifically, EUDRAGIT® S 100, a methyl methacrylate and methacrylic acid copolymer with comonomer ratio of 2:1, respectively, has a dissolution pH of about 7.0, thereby making is suitable for enteric release of rapamycin.

The encapsulated rapamycin nanoparticles may be delivered in various physical entities including a pill, tablet, or capsule. The encapsulated rapamycin nanoparticles may be pressed or formed into a pellet-like shape and further encapsulated with a coating, for instance, an enteric coating. In another embodiment, the encapsulated rapamycin nanoparticles may be loaded into a capsule, also further enterically coated.

Various performance enhancing additives can be added to the encapsulated rapamycin nanoparticles. For example, additives that function as free radical scavengers or stabilizers can be added to improve oxidative and storage stability of the encapsulated rapamycin nanoparticles. Free radical scavengers are preferably chosen from the group that consists of glycerol, propylene glycol, and other lower alcohols. Additives alternatively incorporate antioxidants, such as α-tocopherol (vitamin E), citric acid, EDTA, α-lipoic acid, or the like.

Methacrylic acid copolymers with methyl acrylate or methyl methacrylate are moderate oxygen barriers. Furthermore, these polymers will exhibit an equilibrium moisture content. Oxygen transport due to residual solvent, moisture or other causes, can lead to degradation of the encapsulated rapamycin nanoparticles. Oxygen barrier materials can be added to the encapsulated rapamycin nanoparticles formulation to improve oxygen barrier properties. Preferred oxygen barrier polymers compatible with the preferred polymers are polyvinyl alcohol (PVA) and gelatin.

Preferred Microparticle and Nanoparticle Embodiments

Preferred embodiments with rapamycin nanoparticle inclusions comprise discrete nanoparticles of rapamycin heterogeneously dispersed in a controlled release matrix. As illustrated in accompanying drawings, the rapamycin nanoparticles are prepared by a suitable method and may contain additives to promote nanoparticle stability, modify rapamycin crystallinity, or promote compatibility of the rapamycin nanoparticles with the controlled release matrix. The controlled release matrix is formulated to promote release of rapamycin to specific parts of the body, such as the intestine, to enhance oxidative and storage stability of the encapsulated rapamycin nanoparticles, and to maintain the discrete, heterogeneously distributed nature of the rapamycin nanoparticles.

Rapamycin nanoparticles are preferably prepared by antisolvent precipitation or solidification, also sometimes referred to as controlled precipitation or solidification. Antisolvent solidification is a preferred approach as it provides exquisite control of particle size and distribution, particle morphology, and rapamycin crystallinity. For example, it is possible to prepare nanoparticles with narrow particle size distribution that are amorphous, crystalline, or combinations thereof. Such properties may exhibit additional benefits, by further controlling the biodistribution and bioavailability of rapamycin in specific indications.

Rapamycin is dissolved in a suitable water-miscible solvent 160 and then rapidly injected into rapidly stirred water containing an appropriate aqueous soluble dispersant 110. Water-miscible solvents 160 for rapamycin include methanol, ethanol, isopropyl alcohol, acetone, dimethylsulfoxide, dimethylacetamide, n-methylpyrolidone, tetrahydrofuran, and other solvents. Low boiling point, high vapor pressure water-miscible solvents 160 are preferred to facilitate their removal during subsequent microparticle formation. Some preferred water-miscible solvents 160 are methanol, acetone, and isopropyl alcohol. A preferred water-miscible solvent 160 is methanol. Some aqueous soluble dispersants 110 include ionic surfactants such as sodium dodecyl sulfate and sodium cholate, non-ionic surfactants such as Pluronics, Poloxomers, Tweens, and polymers, such as polyvinyl alcohol and polyvinylpyrolidone. Some preferred aqueous-soluble dispersants 110 are sodium cholate, Pluronic F-68, and Pluronic F-127. A preferred aqueous-soluble dispersant 110 is sodium cholate, which provides surprisingly beneficial properties in the present application.

Not only is sodium cholate a surfactant and a dispersant, it serves to produce multimolecular structures which tend to cause aggregation of rapamycin within those structures, particularly when the pH and other condition of the aqueous solution are controlled to allow aggregation of the rapamycin from that aqueous solution. The resulting process allows for rapamycin nanoparticle production that not only tends to produce nanoparticles in highly predictable size ranges, but also provides a resulting nanoparticle with surprisingly desirable levels of colloidal stability. Moreover, while sodium cholate tends to be a polar molecule as well as an amphoteric surfactant, it induces an ionic charge in each hydrophilic nanoparticle when it is enmeshed in the EUDRAGIT® matrix. It is believed that when the nanoparticle is released from the EUDRAGIT® matrix within the animal subject's enteric passages where conditions are basic, the same properties cause the nanoparticle to be more readily received and absorbed through the intestinal walls.

Rapamycin is dissolved in the water-miscible solvent 160 at a concentration of about 0.01% w/v to about 10.0% w/v preferably about 0.1% w/v to about 1.0% w/v. The aqueous-soluble dispersant 110 is dissolved in water at a concentration above its critical micelle concentration, or CMC, typically at about 1 to about 10 times the CMC. The rapamycin solution is injected into the aqueous-soluble dispersant solution with agitation at a volumetric ratio of about 1:10 to about 1:1, preferably about 1:5 to about 1:1.

The controlled release matrix is prepared from a water-soluble polymer, preferably a copolymer of methacrylic acid with either methyl acrylate or methyl methacrylate, such as those marketed under the trade name of EUDRAGIT® and having pH-dependent dissolution properties. More preferably the controlled release matrix is comprised of EUDRAGIT® S 100, although other water-soluble enteric controlled release would be suitable. Water-soluble controlled release matrices are selected so as either not to compromise the integrity of rapamycin nanoparticles or to provide a medium in which rapamycin nanoparticles may be prepared by the controlled precipitation methodology described previously.

In preparing the water-soluble polymer it is preferable to maintain conditions that do not compromise the integrity of the rapamycin nanoparticles. Firstly, since the rapamycin nanoparticles are susceptible to solubilization by certain co-solvents, it is important to maintain a suitable quantity of certain co-solvents to achieve controlled release matrix solubility while not deleteriously affecting the morphology of the rapamycin nanoparticles. Secondly, rapamycin nanoparticles will be susceptible to chemical degradation by high pH; therefore, it is important to modulate the controlled release matrix solution pH so that rapamycin is not chemically altered. It is preferable the controlled release matrix solution pH be maintained below about pH 8. Lastly, it is preferable to achieve near to complete solubilization of the controlled release matrix in solution so that microencapsulation of the rapamycin nanoparticles by the controlled release matrix in subsequent processing steps may proceed with high efficiency. When using the EUDRAGIT® S 100 as the controlled release matrix, it is preferable to achieve a controlled release matrix solution by using a combination of co-solvents and solution pH modulation. It is preferable the co-solvents be about 40% or less by volume. Similarly, it is preferable that the pH of the controlled release matrix solution be about 8 or less, such that the EUDRAGIT® S 100 is not completely neutralized and is preferably only about 80% or less neutralized. These preferred conditions achieve nearly complete to complete solubilization of the EUDRAGIT® S 100 in a medium that is mostly aqueous and that maintains the integrity of the rapamycin nanoparticles, therefore leading to their microencapsulation by the controlled-release matrix in subsequent processing steps.

The rapamycin nanoparticles prepared by the preferred controlled precipitation method are added to the aqueous solution of the controlled released matrix, resulting in a nanoparticle dispersion in the solubilized controlled release matrix. Alternatively, the rapamycin solubilized in a suitable or preferred co-solvent can be dispersed into the aqueous solution of controlled release matrix leading to controlled precipitation of rapamycin particles, thereby leading to a rapamycin nanoparticle dispersion in fewer processing steps, but of appropriate composition to permit subsequent microencapsulation processing.

As an alternative embodiment, the encapsulated rapamycin nanoparticles are created using pre-existing nanoparticle substrates, such as albumin, to create, in the case of albumin, "albumin-rapamycin nanoparticles." Within this general class of alternatives, preferred approaches for creating the albumin-rapamycin nanoparticles involve encapsulating rapamycin within albumin nanoparticles or preferentially associating rapamycin with albumin nanoparticles through physical or chemical adsorption. The albumin nanoparticles themselves are preferably formed from human serum albumin, a plasma protein derived from human serum.

More particularly, this embodiment preferably involves use of a therapeutic peptide or protein that is covalently or physically bound to albumin, to enhance its stability and half-life. With the albumin stabilized, the rapamycin is mixed with the stabilized albumin in an aqueous solvent and passed under high pressure to form rapamycin-albumin nanoparticles in the size range of 100-200 nm (comparable to the size of small liposomes).

Preferred embodiments also address degradation risks and other limits imposed by the related art by preparing encapsulated rapamycin nanoparticles as a heterogeneous mixture of rapamycin nanoparticles in a polymer matrix. Distributed nanoparticles are morphologically different than homogeneous rapamycin and are less susceptible to degradation because of the bulk nature of the nanoparticles compared to the smaller size of molecular rapamycin.

Another alternative embodiment involves biodegradable polymers loaded with rapamycin. Biodegradable polymers loaded with drugs can be microparticles. "Microparticle" refers to particles between about 0.1 and 300 µm in size. Drug-loaded biodegradable polymers release drug in a time-dependent manner.

As used herein, "biodegradable" refers to any natural means by which a polymer can be disposed of in a patient's body. This includes such phenomena as, without limitation, biological decomposition, bioerosion, absorption, resorption, etc. Biodegradation of a polymer in vivo results from the action of one or more endogenous biological agents and/or conditions such as, without limitation, enzymes, microbes, cellular components, physiological pH, temperature and the like.

In some aspects, the biodegradable polymers can be poly-ε-caprolactone (PCL) microparticles. PCL is a biodegradable, biocompatible, and semicrystalline polymer. PCL is useful for drug delivery because it is highly permeable to many drugs and is non-toxic. Sinha et al. 2004. Rapamycin can also be loaded onto microparticles of other biodegradable polymers, including but not limited to aliphatic polyester, polylactide, polyglycolide, poly(lactide-co-glycolide), mixtures thereof, and their copolymers. Such biodegradable polymers are known in the art.

Rapamycin may be loaded onto microspheres of PCL alone or of PCL copolymers or blends to obtain the desired drug release characteristics. Copolymers of PCL can be formed using many different monomers, including, but not limited to, ethylene oxide, polyvinylchloride, chloroprene, polyethylene glycol, polystyrene, diisocyanates (urethanes), tetrahydrofuran (THF), diglycolide, dilactide, δ-valerolactone, substituted caprolactones, 4-vinyl anisole, styrene, methyl methacrylate, and vinyl acetate.

Drug-loaded PCL microspheres can be prepared by several different methods known by persons of skill in the art, including, but not limited to, and o/w emulsion solvent extraction/evaporation method, a w/o/w emulsion solvent evaporation technique, a spray drying technique, a solution-enhanced dispersion method, and a hot melt technique. These methods are described in more detail in Sinha et al., 2004, which is hereby incorporated by reference. Briefly, as a non-limiting example, the o/w emulsion solvent extraction evaporation method can be performed by dissolving the required amount of polymer and drug in an organic phase, emulsifying under stirring with polyvinyl alcohol to form an o/w emulsion, stirring for 3 hours at about 500 rpm to evaporate the organic phase, and filtering and drying the formed microspheres.

Drug-loaded microspheres of aliphatic polyesters, polylactide, polyglycolide, and poly(lactide-co-glycolide) can be prepared by several different methods known by persons of skill in the art. Non-limiting examples can be found in the following references, all of which are hereby incorporated by reference: Kemala et al., 2012; Ghassemi et al., 2009; Corrigan & Heelan, 2001; Cleland et al., WIPO Pub. No. WO 1995/11009; and Atkins et al., WIPO Pub. No. WO 1995/009613.

In some aspects of this alternative embodiment, the microparticles loaded with rapamycin are encased, encapsulated, or coated to provide for release in the intestinal tract, including the colon.

In some aspects, the microparticles are coated with an enteric coating, which is a coating that prevents release and absorption of active ingredients until they reach the intestine. Some enteric coatings facilitate delivery of agents to the colon. In some embodiments, the enteric coating is a EUDRAGIT® coating. EUDRAGIT® coatings include EUDRAGIT® L 100-55, Poly(methacrylic acid-co-ethyl acrylate) 1:1; EUDRAGIT® L 30 D-55, Poly(methacrylic acid-co-ethyl acrylate) 1:1; EUDRAGIT® L-100, Poly(methacrylic acid-co-methyl methacrylate) 1:1; EUDRAGIT® S 100, Poly(methacrylic acid-co-methyl methacrylate) 1:2; EUDRAGIT® FS 30 D, Poly(methyl acrylate-co-methyl methacrylate-co-methacrylic acid) 7:3:1; EUDRAGIT® RL, Poly(ethyl acrylate-co-methyl methacrylate-co-trimethylammonioethyl methacrylate chloride) 1:2: 0.2; EUDRAGIT® RS, Poly(ethyl acrylate-co-methyl methacrylate-co-trimethylammonioethyl methacrylate chloride) 1:2:0.1; and EUDRAGIT® E, Poly(butyl methacrylate-co-(2-dimethylaminoethyl) methacrylate-co-methyl methacrylate) 1:2:1. Other coatings include EUDRAGIT® RS, EUDRAGIT® RL, ethylcellulose, and polyvinyl acetate. Benefits include pH-dependent drug release, protection of active agents sensitive to gastric fluid, protection of gastric mucosa from active agents, increase in drug effectiveness, good storage stability, and GI and colon targeting, which minimizes risks associated with negative systemic effects and maintains effective dosing.

In some aspects, colon targeting of rapamycin can be achieved by creating PCL microparticles loaded with rapamycin or rapamycin analog and subsequently coating the microparticles with EUDRAGIT® S 100. Methods of making such coated microparticles can be found in Ghorab et al., 2011, which is hereby incorporated by reference. Briefly, drug-loaded PCL microparticles are suspended in a solution containing an appropriate amount of EUDRAGIT® S 100 dissolved in ethyl alcohol. The suspension is poured into distilled water. The resulting mixture is homogenized for five minutes and then mechanically stirred until the organic solvent is completely evaporated. Microparticles are collected, washed with cyclohexane twice, and dried overnight in a dessicator.

Some other examples of enteric coating components include cellulose acetate phthalate, methyl acrylate-methacrylic acid copolymers, cellulose acetate succinate, hydroxyl propyl methyl cellulose phthalate, hydroxyl propyl methyl cellulose acetate succinate, polyvinyl acetate phthalate, methyl methacrylate-methacrylic acid copolymers, sodium alginate, and stearic acid. The coating may include suitable hydrophilic gelling polymers including, but not limited to, cellulosic polymers, such as methylcellulose, carboxymethylcellulose, hydroxypropylcellulose, hydroxypropylmethylcellulose, hydroxyethylcellulose, and the like; vinyl polymers, such as polyvinylpyrrolidone, polyvinyl alcohol, and the like; acrylic polymers and copolymers, such as acrylic acid polymer, methacrylic acid copolymers, ethyl acrylate-methyl methacrylate copolymers, natural and synthetic gums, such as guar gum, arabic gum, xanthan gum, gelatin, collagen, proteins, polysaccharides, such as pectin, pectic acid, alginic acid, sodium alginate, polyamino acids, polyalcohols, polyglycols, and the like; and mixtures thereof. Any other coating agent known to those of ordinary skill in the art is contemplated for inclusion in the coatings of the microcapsules set forth herein.

The coating may optionally comprise a plasticizer, such as dibutyl sebacate, polyethylene glycol and polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof. The coating may optionally include a gum. Non-limiting examples of gums include homopolysaccharides such as locust bean gum, galactans, mannans, vegetable gums such as alginates, gum karaya, pectin, agar, tragacanth, *acacia*, carrageenan, chitosan, alginic acid, other polysaccharide gums (e.g., hydrocolloids), *acacia catechu*, salai guggal, indian bdellium, copaiba gum, asafetida, cambi gum, *Enterolobium cyclocarpum*, mastic gum, benzoin gum, sandarac, gambier gum, *Butea frondosa* (Flame of Forest Gum), myrrh, konjak mannan, guar gum, welan gum, gellan gum, tara gum, locust bean gum, carrageenan gum, glucomannan, galactan gum, sodium alginate, xanthan gum, deacetylated xanthan gum, pectin, sodium polypectate, gluten, karaya gum, tamarind gum, ghatti gum, Acaroid/Yacca/Red gum, dammar gum, juniper gum, ester gum, ipil-ipil seed gum, gum talha (*acacia seyal*), and cultured plant cell gums including those of the plants of the genera: *Acacia, Actinidia, Aptenia, Carpobrotus, Cichorium, Cucumis, Glycine, Hibiscus, Hordeum, Letuca, Lycopersicon, Malus, Medicago, Mesembryanthemum, Oryza, Panicum, Phalaris,*

*Phleum*, Poliathus, Polycarbophil, *Sida, Solanum, Trifolium, Trigonella, Afzelia africana* seed gum, *Treculia africana* gum, detarium gum, *cassia* gum, carob gum, *Prosopis africana* gum, Colocassia esulenta gum, *Hakea gibbosa* gum, khaya gum, scleroglucan, *zea*, mixtures of any of the foregoing, and the like.

A variety of other encasing materials and systems for delivering rapamycin-loaded biodegradable microspheres to the colon can be used alone or in combination with a pH-dependent coating like EUDRAGIT® S 100. Non-limiting examples follow.

Hydrophilic gelling polymers or copolymers can be included in a material encasing one or more microspheres to provide a time-dependent release of drug-loaded microspheres. Non-limiting examples of hydrophilic gelling copolymers include methylcellulose, carboxymethylcellulose, hydroxypropylcellulose, hydroxypropylmethylcellulose, carbomers, polyvinyl alcohols, polyoxyethylene glycols, polyvinylpyrrolidones, poloxamers, or natural or synthetic rubbers. An intermediate layer of these polymers can be included to delay release of active ingredient for a desired amount of time, as described in Poli et al., (EP0572942). Another example of a time-dependent encasing material is a wax matrix including, for example, behenic acid, as described in Otuska & Matsuda, 1994.

Polysaccharides that are resistant to digestive enzymes but are enzymatically broken down by bacteria in the colon can be included in an encasing material. Non-limiting examples include chitosan and pectin as described in Coulter (EP2380564), and azopolymers, disulfide polymers, amylose, calcium pectinate, and chondroitin sulfate as described in Watts (EP0810857).

A starch capsule coated with an enteric coating such as EUDRAGIT® S 100 or EUDRAGIT® L 100 may be used, as described in Watts (EP0180857). A variety of starches, including modified starches and starch derivatives may be used. Non-limiting examples include hydroxyethyl starch, hydroxypropyl starch, carboxymethyl starch, cationic starch, acetylated starch, phosphorylated starch, succinate derivatives, or grafted starches.

A layer of insoluble or relatively insoluble rupturable polymer can be used as part of a strategy to provide for abrupt release of drug-loaded microspheres in the colon. The rupturable polymer can comprise one or more of a variety of suitable polymers known by those of skill in the art, including, but not limited to, cellulose acetate, cellulose acetate propionate, or ethyl cellulose. A variety of strategies for causing rupture of the polymer in the colon can be employed. As a non-limiting example, the rupturable polymer can be designed to rupture upon encountering increased pressure due to intestinal peristalsis, as described in Muraoka et al., 1998. As another example, the rupturable polymer can be semi-permeable, and an effervescent solid can be included in a core containing the drug-loaded microparticles, as described in Krogel & Bodmeier, 1999. As another example, a layer of swellable material, including, but not limited to, croscarmellose sodium or hydroxypropylmethyl cellulose, can be disposed within the rupturable polymer layer, as described in Bussemer et al., 2001. Controlled entry of water past the rupturable polymer layer can be provided by embedded hydrophilic particulate material, as described in Lerner et al., (WIPO Pub. No. WO 1999/018938).

A two-piece encasing system, as described in McNeill et al., (WIPO Pub. No. WO 1990/009168) can be used to provide for release of drug-loaded microspheres in the colon. One of the pieces is a relatively water insoluble capsule with an open orifice, which is covered by a second piece that swells as it takes up water. The swelling causes displacement from the orifice and release of the capsule contents.

Examples of Preferred mTOR Inhibiting Preparations

Example 1—Development of methods to produce rapamycin nanoparticles. Rapid solvent exchange was used to examine the formation of rapamycin nanoparticles. Three water-miscible solvents 160 and three water-soluble surfactants were selected to study their respective effects on the formation and morphology of rapamycin nanoparticles. The water-miscible solvents 160 were isopropyl alcohol (Solvent 1), acetone (Solvent 2), and methanol (Solvent 3). The water-soluble surfactants were Pluronic F-68 (Dispersant 1, a non-ionic PEO-PPO-PEO block copolymer), Pluronic F-127 (Dispersant 2, a non-ionic PEO-PPO-PEO block copolymer), and sodium cholate (Dispersant 3, an anionic surfactant). Rapamycin was dissolved in each of the water-miscible solvents 160 at a concentration of 0.25% w/v. The water-soluble surfactants were dissolved in deionized water at concentrations of 0.5% w/v, 0.5% w/v, and 1.0% w/v, respectively, for each of the dispersants. Each experimental combination (e.g. NP-1 to NP-9 in following table) consisted of 5 mL of rapamycin solution and 25 mL of surfactant solution, resulting in a dilution factor of 1:5 solvent:water. 25 mL of surfactant solution was transferred to a 50 mL beaker and stirred with the aid of magnetic micro stir bar. Rapamycin solution was rapidly injected at 500 µL increments with the aid of a micropipette with the pipette tip placed below the surface of the rapidly stirred surfactant solution. The visual appearance of the resulting nanoparticles and their colloidal stability after 24-hours were qualitatively assessed. The following table summarizes the qualities of the rapamycin nanoparticle dispersions. Qualitatively, rapamycin nanoparticle dispersions having a colorless to blue, opalescent appearance will have particle sizes on the order of less than about 300 nm as evidenced by their interaction with the ultraviolet wavelengths of visible light. Whereas, dispersions having a more white appearance will have particle sizes larger than about 300 nm due to their interaction with the broader spectrum of visible light. Rapamycin nanoparticle formulations NP-7 and NP-9 were selected as preferred methods of nanoparticle preparation.

|  | Dispersant 1 | Dispersant 2 | Dispersant 3 |
|---|---|---|---|
| Solvent 1 | NP-1: White, settled, redispersible | NP-2: Blue, opalescent, settled, redispersible | NP-3: Clear, aggregated, redispersible |
| Solvent 2 | NP-4: Blue, opalescent, some settling | NP-5: White, settled, redispersible | NP-6: Blue, opalescent, settled, redispersible |
| Solvent 3 | NP-7: Blue, opalescent, stable | NP-8: Blue to white, settled, redispersible | NP-9: Blue, opalescent, stable |

Example 2—Preparation of a high concentration rapamycin nanoparticle dispersion. The water-miscible solvent 160 and water-soluble dispersant 110 of NP-9 from Example 1 was used to prepare rapamycin nanoparticles. 656 mg of rapamycin were dissolved in 6.56 mL of Solvent 3 to yield a 1.0% w/v solution. This volume of rapamycin solution was injected into 26.25 mL of 1.0% w/v Dispersant 1 in deionized water. The resulting rapamycin nanoparticle dispersion had a final rapamycin content of 2.4% w/w. The particle size of the dispersion was determined by dynamic light scattering to be 230 nm±30 nm with a single peak.

Example 3—Preparation of a water-soluble enteric coating. 3.5 g of EUDRAGIT® S 100 were added to 70 mL of deionized water with light stirring, resulting in a white dispersion. 1.4 g of sodium hydroxide were added to the dispersion with continued stirring. The resulting dispersion gradually turned clear and colorless indicating an aqueous solution of S-100. The estimated concentration of sodium hydroxide was 0.5N.

Example 4—Preparation of a feedstock containing rapamycin nanoparticles and a water-soluble enteric coating. Rapamycin nanoparticles were prepared as described in Example 2 and then slowly added to an aqueous solution of EUDRAGIT® S 100 prepared as in Example 3. The ratio of rapamycin to EUDRAGIT® S 100 was 1:9, or 10% wt. rapamycin payload. The resulting dispersion was allowed to stir for several minutes to observe stability. After one hour, the dispersion had transformed to a clear yellow, indicating destruction of the rapamycin nanoparticles and a change in the rapamycin. Addition of a small amount of acetic acid to reduce the solution pH to below neutral resulted in a clear, colorless solution.

Example 5—Preparation of water-soluble enteric coating with a water-miscible co-solvent. 3.5 g of EUDRAGIT® S 100 were added to 30/70 v/v methanol/deionized water, resulting in a white dispersion. The dispersion was stirred continuously until a clear solution was formed.

Example 6—Preparation of a feedstock containing rapamycin nanoparticles and a water-soluble enteric coating. Rapamycin nanoparticles were prepared as described in Example 2 and then slowly added to an aqueous solution of EUDRAGIT® S 100 prepared as in Example 5. The ratio of rapamycin to S 100 was 1:9, or 10% wt. rapamycin payload. The white dispersion was allowed to stir for several minutes after which the dispersion was transformed into a clear solution indicating the rapamycin nanoparticles had been destroyed.

Example 7—Preparation of a partially-neutralized, water-soluble enteric coating with a water-miscible co-solvent. 3.5 g of EUDRAGIT® S 100 were added to 10/90 v/v methanol/deionized water, resulting in a white dispersion. The dispersion was titrated to clarity with 2.000 mL of 4.8M sodium hydroxide. The estimated neutralization of the S-100 was 78%.

Example 8—Preparation of a feedstock containing rapamycin nanoparticles and a water-soluble enteric coating. Rapamycin nanoparticles were prepared as described in Example 2 then slowly added to an aqueous solution of EUDRAGIT® S 100 as prepared in Example 7. The ratio of rapamycin to EUDRAGIT® S 100 was 1:9, or 10% wt. rapamycin payload. The resulting white dispersion remained stable for several hours as indicated by no change in color or change in optical clarity. The final pH was 7.5. The particle size of the final dispersion was determined by dynamic light scattering to be 756 nm±52 nm with a single peak and indicating possible clustering of the rapamycin nanoparticles in the resulting feedstock.

Example 9—Preparation of a feedstock containing rapamycin nanoparticles and a water-soluble enteric coating. The rapamycin solution used in Example 2 was injected, with stirring, into the aqueous solution of EUDRAGIT® S 100 prepared in Example 7. The ratio of rapamycin to EUDRAGIT® S 100 was 1:9, or 10% wt. rapamycin payload. A blue, opalescent colloid was formed and it remained stable for several hours as indicated by no change in color or change in optical clarity. The final pH was 7.5. The particle size of the final dispersion was determined by dynamic light scattering to be 305 nm±60 nm with a single peak.

Example 10—Spray drying of feedstock containing rapamycin nanoparticles and a water-soluble enteric coating. The feedstocks prepared in Examples 8 and 9 were spray dried and analyzed for rapamycin content. Particles prepared from Example 8 had a rapamycin content of 9.5% wt. (87% rapamycin yield). Particles prepared from Example 9 had a rapamycin content of 7.9% wt. (80% rapamycin yield).

Example 11—Storage stability of enteric-coated encapsulated rapamycin nanoparticles. Microparticles prepared by spray drying in Example 10 were stored under controlled conditions at room temperature and 50% relative humidity. Samples were analyzed weekly for rapamycin content. All samples maintained at least 95% of their original rapamycin content at all time points for at least three weeks.

Figure 4:
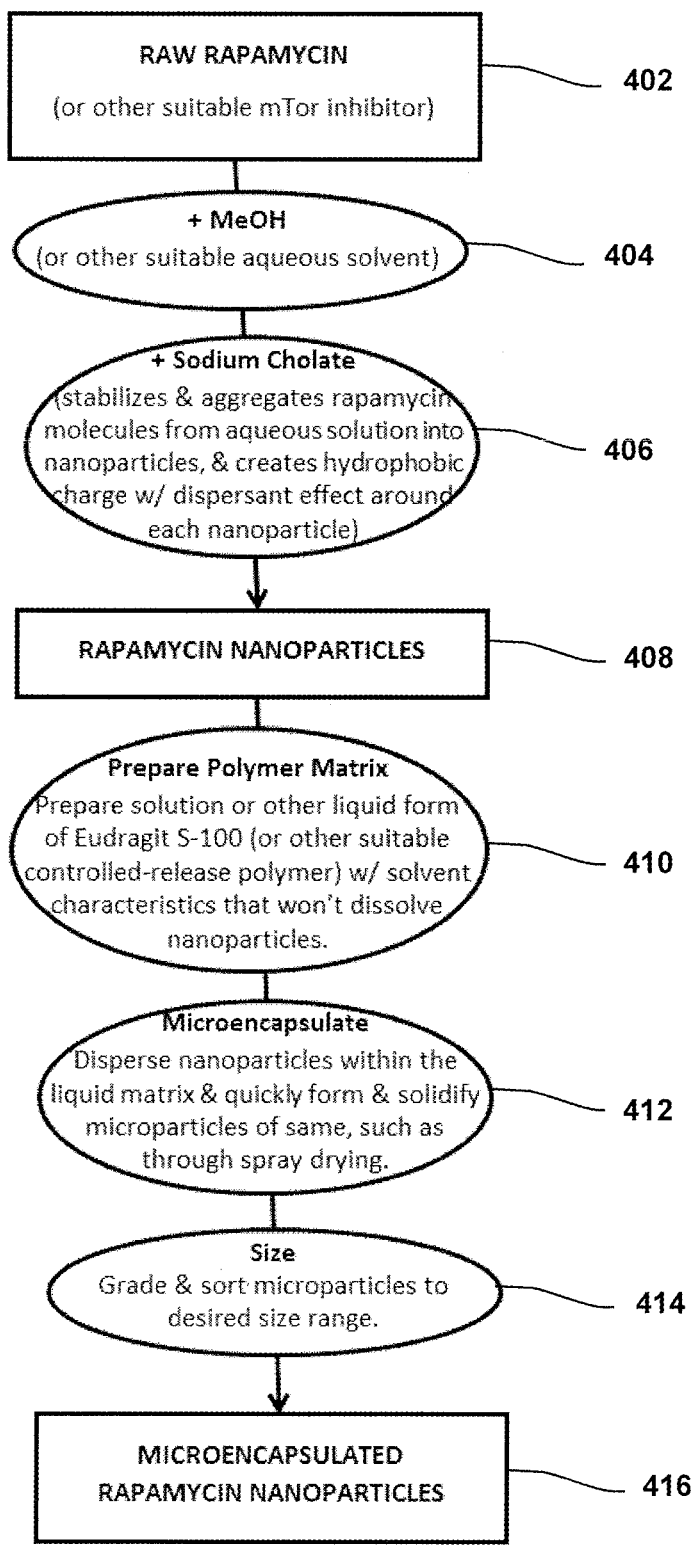
FIG. 4 is a flowchart illustrating detailed steps of a more comprehensive preferred process for producing preferred forms of enteric-coated rapamycin nanoparticles, which includes the process for producing a nanoparticle dispersion as illustrated in FIG. 2, together with additional steps for microencapsulating the rapamycin nanoparticles.

Example 12—Preparation of nanoparticles in EUDRAGIT® S 100 as illustrated in FIGS. 4A & 4B. A rapamycin solution was prepared by combining rapamycin with methanol (at Steps 402 & 404) in a 10% w/v ration as 3.03 g rapamycin and 30.25 mL methanol. A 1% w/w sodium cholate solution was prepared by combining 1.2 g sodium cholate with 120 mL deionized water as shown in Step 424. Nanoparticle formation was achieved by transferring the rapamycin solution with a 60 mL plastic syringe equipped with a 20 ga needle, injecting the rapamycin solution below the surface of the sodium cholate solution in a 250 mL beaker (Steps 406 & 408). Mixing was accomplished with a paddle mixer operating at 300 rpm yielding a rapamycin nanoparticle suspension. At Step 410, a 10% w/w EUDRAGIT® S 100 solution was prepared by combining 20 g EUDRAGIT® S 100 in a 9.7% w/v mixture with 180 mL deionized water, 25.72 mL methanol in a 12.5% v/v mixture, and 1.8 g sodium cholate in a 0.875% w/v mixture. This 10% w/w EUDRAGIT® S 100 solution was titrated with 4M sodium hydroxide to achieve a pH of between about 7.5 and about 7.6. Encapsulated rapamycin particles were then fabricated by combining the EUDRAGIT® S 100 solution with the rapamycin nanoparticle suspension at Step 412. The EUDRAGIT® S 100 solution and the rapamycin nanoparticle suspension were combined in a 500 mL bottle, adding 2.13 g of glycerol and mixing with a magnetic stir bar. The combined EUDRAGIT® S 100 solution and rapamycin nanoparticle suspension were then spray dried and collected. The spray drying parameters (shown at Step 418) included a 0.4 mm nozzle, nozzle air pressure of 3 bar, input air temperature of 110° C., a sample pump rate of 5 mL/min and an air speed of 0.30 m3/min. After the preferred nanoparticle microencapsulation process is complete, the nanoparticles may then be graded and sorted according to the desired size range at Step 414. Alternatively, the resulting dispersion of rapamycin nanoparticles in the controlled release matrix solution can be reduced to a dry particulate powder by a suitable process, thereby resulting in microparticles of a heterogeneous nature comprised of rapamycin nanoparticles randomly distributed in the controlled release matrix. This dry particulate powder can then be combined with excipients and pressed into tablet form as indicated at Step 420.

Methods of Using Rapamycin Compositions

"Treatment" and "treating" refer to administration or application of a therapeutic agent to a subject or performance of a procedure or modality on a subject for the purpose of obtaining a therapeutic benefit for a disease or health-related condition. For example, the rapamycin compositions of the present invention may be administered to a subject for the purpose of treating or preventing intestinal adenomas or polyps and cancer in a patient who has been identified as being at risk for developing intestinal polyps or intestinal cancer.

The terms "therapeutic benefit," "therapeutically effective," or "effective amount" refer to the promotion or enhancement of the well-being of a subject. This includes, but is not limited to, a reduction in the frequency or severity of the signs or symptoms of a disease.

"Prevention" and "preventing" are used according to their ordinary and plain meaning. In the context of a particular disease or health-related condition, those terms refer to administration or application of an agent, drug, or remedy to a subject or performance of a procedure or modality on a subject for the purpose of preventing or delaying the onset of a disease or health-related condition. For example, one embodiment includes administering the rapamycin compositions of the present invention to a subject at risk of developing intestinal polyps and cancer (e.g., a patient who has been diagnosed with FAP) for the purpose of preventing intestinal polyps and cancer.

Rapamycin compositions, as disclosed herein, including preferably encapsulated rapamycin nanoparticles, may be used to prevent, treat, delay or reduce any disease or condition (or its precursors or sequelae) for which an inhibitor of mTOR is contemplated as effective for treatment, prevention, or delaying or reducing its progression. For example, methods are disclosed herein of using rapamycin compositions to treat or prevent diseases or conditions which a patient has been identified as being at risk for developing, including: intestinal polyps or intestinal cancer, such as colorectal cancer or FAP; vascular cognitive impairment; canine hemolytic anemia; and feline chronic gingivostomatitis (FCGS) and other gum and gingival diseases.

Other uses of rapamycin compositions, as disclosed herein, including preferably encapsulated rapamycin nanoparticles, are also contemplated. For example, U.S. Pat. No. 5,100,899 discloses inhibition of transplant rejection by rapamycin; U.S. Pat. No. 3,993,749 discloses rapamycin antifungal properties; U.S. Pat. No. 4,885,171 discloses antitumor activity of rapamycin against lymphatic leukemia, colon and mammary cancers, melanocarcinoma and ependymoblastoma; U.S. Pat. No. 5,206,018 discloses rapamycin treatment of malignant mammary and skin carcinomas, and central nervous system neoplasms; U.S. Pat. No. 4,401,653 discloses the use of rapamycin in combination with other agents in the treatment of tumors; U.S. Pat. No. 5,078,999 discloses a method of treating systemic lupus erythematosus with rapamycin; U.S. Pat. No. 5,080,899 discloses a method of treating pulmonary inflammation with rapamycin that is useful in the symptomatic relief of diseases in which pulmonary inflammation is a component, i.e., asthma, chronic obstructive pulmonary disease, emphysema, bronchitis, and acute respiratory distress syndrome; U.S. Pat. No. 6,670,355 discloses the use of rapamycin in treating cardiovascular, cerebral vascular, or peripheral vascular disease; U.S. Pat. No. 5,561,138 discloses the use of rapamycin in treating immune related anemia; U.S. Pat. No. 5,288,711 discloses a method of preventing or treating hyperproliferative vascular disease including intimal smooth muscle cell hyperplasia, restenosis, and vascular occlusion with rapamycin; and U.S. Pat. No. 5,321,009 discloses the use of rapamycin in treating insulin dependent diabetes mellitus.

Pharmaceutical Preparations

Certain methods and compositions set forth herein are directed to administration of an effective amount of a composition comprising the rapamycin compositions of the present invention.

1. Compositions

A "pharmaceutically acceptable carrier: includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present invention may comprise different types of carriers depending on whether it is to be administered in solid, liquid or aerosol form, and whether it needs to be sterile for such routes of administration as injection.

The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations should meet sterility, pyrogenicity, and general safety and purity standards as required by FDA Office of Biologics standards.

The formulation of the composition may vary depending upon the route of administration. For parenteral administration in an aqueous solution, for example, the solution should be suitably buffered if necessary and the liquid diluent first rendered isotonic with sufficient saline or glucose. In this connection, sterile aqueous media that can be employed will be known to those of skill in the art in light of the present disclosure.

In addition to the compounds formulated for parenteral administration, such as intravenous or intramuscular injection, other pharmaceutically acceptable forms include, e.g., tablets or solids for oral administration; liposomal and nanoparticle formulations; enteric coating formulations; time release capsules; formulations for administration via an implantable drug delivery device; and any other form. One may also use nasal solutions or sprays, aerosols or inhalants in the present invention.

The capsules may be, for example, hard-shell capsules or soft-shell capsules. The capsules may optionally include one or more additional components that provide for sustained release.

In certain embodiments, pharmaceutical composition includes at least about 0.1% by weight of the active compound. In other embodiments, the pharmaceutical composition includes about 2% to about 75% of the weight of the composition, or between about 25% to about 60% by weight of the composition, for example, and any range derivable therein.

The compositions may comprise various antioxidants to retard oxidation of one or more components. Additionally, the prevention of the action of microorganisms can be accomplished by preservatives such as various antibacterial and antifungal agents, including, but not limited to, parabens (e.g., methylparabens, propylparabens), chlorobutanol, phenol, scorbic acid, thimerosal or combinations thereof. The composition should be stable under the conditions of manufacture and storage, and preserved against the contaminating action of microorganisms, such as bacteria and fungi.

In certain preferred embodiments, an oral composition may comprise one or more binders, excipients, disintegration agents, lubricants, flavoring agents, and combinations thereof. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, EUDRAGIT® Acrylic Drug Deliver Polymers, or any combination thereof.

In particular embodiments, prolonged absorption can be brought about by the use in the compositions of agents delaying absorption, such as, for example, aluminum monostearate, gelatin, EUDRAGIT® Acrylic Drug Deliver Polymers or combinations thereof.

2. Routes of Administration

Upon formulation, solutions will be administered in a manner compatible with the dosage formulation and in such amount as is therapeutically effective.

The composition can be administered to the subject using any method known to those of ordinary skill in the art. For example, a pharmaceutically effective amount of the composition may be administered intravenously, intracerebrally, intracranially, intraventricularly, intrathecally, into the cortex, thalamus, hypothalamus, hippocampus, basal ganglia, substantia nigra or the region of the substantia nigra, cerebellum, intradermally, intraarterially, intraperitoneally, intralesionally, anally, subcutaneously, orally, topically, locally, by inhalation (e.g., aerosol inhalation (injection, infusion, continuous infusion, localized perfusion bathing target cells directly, via a catheter, via a lavage, in creams, in lipid compositions (e.g., liposomes), or by other method or any combination of the foregoing as would be known to one of ordinary skill in the art (Remington's, 1990).

In particular embodiments, the composition is administered to a subject using a drug delivery device. Any drug delivery device is contemplated for use in delivering an effective amount of the inhibitor of mTOR or mTOR Complex 1(mTORC1).

3. Dosage

A pharmaceutically effective amount of an inhibitor of mTORC1 is determined based on the intended goal. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

The amount of rapamycin or rapamycin analog or derivative to be administered will depend upon the disease to be treated, the length of duration desired and the bioavailability profile of the implant, and site of administration. Generally, the effective amount will be within the discretion and wisdom of the patient's physician. Guidelines for administration include dose ranges of from about 0.01 mg to about 500 mg of rapamycin or rapamycin analog.

For example, a dose of the inhibitor of mTORC1 may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The dose can be repeated as needed as determined by those of ordinary skill in the art. Thus, in some embodiments of the methods set forth herein, a single dose is contemplated. In other embodiments, two or more doses are contemplated. In some embodiments, the two or more doses are the same dosage. In some embodiments, the two or more doses are different dosages. Where more than one dose is administered to a subject, the time interval between doses can be any time interval as determined by those of ordinary skill in the art. For example, the time interval between doses may be about 1 hour to about 2 hours; about 2 hours to about 6 hours; about 6 hours to about 10 hours; about 10 hours to about 24 hours; about 1 day to about 2 days; about 1 week to about 2 weeks, or longer, or any time interval derivable within any of these recited ranges. In specific embodiments, the composition may be administered daily, weekly, monthly, annually, or any range therein.

Doses for encapsulated rapamycin (enteric-coated rapamycin) and for encapsulated rapamycin nanoparticles may be different. According to preferred embodiments of the present invention, doses are contemplated in a range of more than 50 micrograms and up to (or even exceeding) 200 micrograms per kilogram for daily administration, or the equivalent for other frequencies of administration. Although dosing may vary based on particular needs and preferred treatment protocols according to physician preference, maximum tolerable daily bioavailable dosings (trough levels) for a 28-day duration are about 200 micrograms of rapamycin (or equivalent) per subject kilogram, for both human and canine subjects, although those of ordinary skill would understand that greater dose amount ranges would be tolerable and suitable when administered less often than once per day, and lesser ranges would be tolerable when administered more often than once per day.

In certain embodiments, it may be desirable to provide a continuous supply of a pharmaceutical composition to the patient. This could be accomplished by catheterization, followed by continuous administration of the therapeutic agent. The administration could be intra-operative or post-operative.

4. Secondary and Combination Treatments

Certain embodiments provide for the administration or application of one or more secondary or additional forms of therapies. The type of therapy is dependent upon the type of disease that is being treated or prevented. The secondary form of therapy may be administration of one or more secondary pharmacological agents that can be applied in the treatment or prevention of, for example, intestinal polyps or cancer or a disease, disorder, or condition associated with intestinal polyps and cancer in a patient who has been identified as being at risk for developing intestinal polyps or intestinal cancer. Other secondary forms of therapy may be administration of one or more secondary pharmacological agents that can be applied in the treatment or prevention of vascular cognitive impairment or a disease, disorder, or condition associated with vascular pathology or vascular cognitive impairment. For example, the secondary or additional form of therapy may be directed to treating high blood pressure, high cholesterol, high blood sugar (or diabetes), an autoimmune disease, an inflammatory disease, a cardiovascular condition, or a peripheral vascular condition.

If the secondary or additional therapy is a pharmacological agent, it may be administered prior to, concurrently, or following administration of the inhibitor or mTORC1.

The interval between administration of the inhibitor of mTORC1 and the secondary or additional therapy may be any interval as determined by those of ordinary skill in the art. For example, the inhibitor of mTORC1 and the secondary or additional therapy may be administered simultaneously, or the interval between treatments may be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 hours to about 24 hours of each other and, more preferably, within about 6 hours to about 12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In some embodiments, the timing of administration of a secondary therapeutic agent is determined based on the response of the subject to the inhibitor of mTORC1.

5. Kits

Kits are also contemplated as being used in certain aspects of the present invention. For instance, a rapamycin composition of the present invention can be included in a kit. A kit can include a container. Containers can include a bottle, a metal tube, a laminate tube, a plastic tube, a dispenser, a pressurized container, a barrier container, a package, a compartment, or other types of containers such as injection- or blow-molded plastic containers into which the hydrogels are retained. The kit can include indicia on its surface. The indicia, for example, can be a word, a phrase, an abbreviation, a picture, or a symbol.

Further, the rapamycin compositions of the present invention may also be sterile, and the kits containing such compositions can be used to preserve the sterility. The compositions may be sterilized via an aseptic manufacturing process or sterilized after packaging by methods known in the art.

General Uses of the Oral mTOR Preparations

When orally administered daily, or at other regular frequencies, in correspondingly effective doses, pharmaceutical preparations prepared according to the foregoing descriptions, and their equivalents, are effective for preventing and treating various maladies in humans and other animals, and for reducing the progression of those maladies and their sequelae. For example, such oral administration enables a human subject or his/her caregiver to prevent or treat various cancer conditions and neurological conditions, and precursors and sequelae thereof in humans.

Preferably, preparations according to the preferred embodiments are administered at a regular frequency, preferably at frequencies varying from three times per week (either on three consecutive days, or on three regularly distributed days of the week).

Although dosing may vary based on particular needs and preferred treatment protocols according to physician preference, maximum tolerable daily bioavailable dosings (trough levels) for a 28-day duration are about 200 micrograms of rapamycin (or equivalent) per subject kilogram, for both human and canine subjects, although those of ordinary skill would understand that greater dose amount ranges would be tolerable and suitable when administered less often than once per day, and lesser ranges would be tolerable when administered more often than once per day.

Whereas prior art uses of rapamycin may have involved recommended daily dosings of roughly 13 micrograms per kilogram in human subjects, oncology protocols according to preferred embodiments of the present invention use higher dosings than the prior art, preferably in a range of more than 50 micrograms and up to (or even exceeding) 200 micrograms per kilogram for daily administration, or the equivalent for other frequencies of administration. Other conditions addressed by oral administration protocols of the present invention include preventing and treating gingival diseases in humans, dogs and cats, whether through the preferred preparations of rapamycin (or the equivalent) or through combination therapies with stem cell therapy and/or other active pharmaceutical or botanical treatment protocols.

In contrast to oncology-related dosings, preferred protocols for oral administration of the preparations taught herein when used for prevention and treatment of targeted neurological conditions, and reducing the progression thereof, use lower dosings than the prior art. Such lower dosings are preferably about 5 micrograms of bioavailable rapamycin (or the equivalent) per daily oral dose, and such dosings otherwise more generally fall in the preferred range of between 1 and 7 micrograms per kilogram for once-daily administration, or the equivalent for other frequencies of administration.

Although various neurological indications are targeted in alternative embodiments, preferred embodiments of oral administration protocols according to the present invention are used for preventing and treating, and reducing the progression of, Alzheimer's disease, pre-Alzheimer's disease, vascular dementia and other variations of cognitive impairment in general, in humans, canines, felines and other animal subject types. Other neurologic conditions for which embodiments of the present invention are thought to be effective also include the treatment and therapy for traumatic brain injury and traumatic spinal cord injury as well as the prevention and delay of their advancement and sequelae. Such embodiments include preventing and treating anxiety disorders in canines and felines, as well as reducing the progression of neurological impairment in human subjects exhibiting indications related to Alzheimer's disease, vascular dementia, or precursors to onset of Alzheimer's disease.

Specific Uses of Oral mTOR Preparations

The following disclosures describe uses of oral mTOR preparations for specific maladies, and the teachings of the present invention contemplate use of microencapsulated rapamycin nanoparticle preparations for these same purposes. In combination with background information regarding these maladies are specific example descriptions as observed by the inventors and their collaborators.

A. Intestinal Cancer and Familial Adenomatous Polyposis (FAP)

Particularly beneficial results are appreciated through oral administration in the prevention and treatment of familial adenomatous polyposis (FAP), as well as colon cancer and other sequelae of FAP, particularly in human subjects who are identified as being genetically predisposed to develop FAP. Particular benefits are also appreciated in reducing and preventing the progression of FAP and in preventing or delaying the need for colonic resection which is often required before the age of 25 years in humans with FAP.

1. Intestinal Cancer

Intestinal cancer encompasses a variety of cancers, including cancer of the small intestine, gastric cancer, and colorectal cancer. Symptoms of intestinal cancer often include, but are not limited to, pain throughout the body, unexplained weight loss, pain or cramping in the middle of the abdomen, a lump in the abdomen, blood in the stool, nausea, bloating, iron-deficient anemia, and jaundice. Historically, the most common treatment of intestinal cancer is surgery and radiation therapy.

Intestinal cancer is more likely to occur in some patients than others. For example, intestinal cancer is more likely to occur in a patient that has been diagnosed with an inflammatory bowel disease, an intestinal polyp or an adenoma, familial adenomatous polyposis (FAP), or as having a mutation which is known to cause increased WNT signaling. In other embodiments, the patient has a family history of intestinal polyps or intestinal cancer.

Small intestine cancer can be further divided into a variety of subtypes, including cancer of the jejunum and ileum, duodenal cancer, adenocarcinoma, gastrointestinal stromal tumors, lymphoma, and ileal carcinoid tumors. Adenocarcinoma is a type of cancer that begins in the lining of the small intestine, and makes up 40-50% of all small intestinal cancers. This type of intestinal cancer occurs most often later in life. People with Crohn's Disease and certain other inherited conditions such as familial adenomatous polyposis (FAP) and Peutz-Jeghers Syndrome are at higher risk of developing adenocarcinomas. Carcinoid tumors occur when neuroendocrine cells grow abnormally, and may also be referred to as neuroendocrine tumors or neuroendocrine cancer. People with a family history of multiple endocrine neoplasia or a family history of neurofibromatosis are more likely to get carcinoid tumors. Carcinoid tumors are also more common among women, African Americans, and people with certain diseases that damage the stomach and reduce the amount of stomach acid. Gastrointestinal stromal tumors start in the interstitial cells of Cajal (ICCs) in the walls of the GI tract. It is believed that a family history of neurofibromatosis or familial gastrointestinal stromal tumor syndrome will increase a patient's risk of getting stromal tumors. Gastrointestinal lymphomas are a cancer of the lymphatic system that begins in the lymphoid tissue. It is believed that old age, genetic risk factors that cause abnormal function of the immune system, a diet high in animal fat and low in fruits and vegetables, exposure to radiation and certain chemicals, immune deficiencies, and some infections increase the likelihood of a lymphoma developing.

Colorectal cancer, commonly also known as colon cancer or bowel cancer, is a cancer from uncontrolled cell growth in the colon, rectum, or appendix. The majority of colorectal cancers are due to lifestyle and increasing age, but some are associated with an underlying genetic disorder. For example, people with inflammatory bowel disease (ulcerative colitis and Crohn's Disease) are at increased risk for developing colon cancer. Those with a family history of colorectal cancer in two or more first-degree relatives have a two to threefold greater risk of disease, and a number of genetic syndromes are also associated with higher rates of colorectal cancer. The most common of these is hereditary nonpolyposis colorectal cancer (HNPCC or Lynch syndrome) which is present in about 3% of people with colorectal cancer. Other syndromes that are strongly associated include: Gardner syndrome and FAP.

Gastric cancer refers to cancer arising from any part of the stomach, and is often either asymptomatic or causes only nonspecific symptoms in its early stages. Infection by *Helicobacter pylori* is believed to be the cause of most stomach cancer while autoimmune atrophic gastritis, intestinal metaplasia, and various genetic factors are associated with increased risk levels. A very important but preventable cause of gastric cancer is tobacco smoking. Gastric cancers due to smoking mostly occur in the upper part of the stomach near the esophagus.

2. Familial Adenomatous Polyposis (FAP)

Familial adenomatous polyposis (FAP) is an autosomal dominant disease caused by mutation of the adenomatous polyposis coli (APC) gene, located on chromosome 5 (Kinzler, 1991). This germ line defect accelerates the initiation of the adenoma-carcinoma, resulting in the development of numerous adenomatous colorectal polyps at a young age. Polyposis inevitably progresses to colorectal cancer if left untreated. Given the predictable development of colorectal cancer in patients with FAP, the safest preventative strategy is surgical resection of the colon when polyposis develops. The two main prophylactic surgeries are colectomy with ileorectal anastomosis (IRA) and proctocolectomy with ileal pouch-anal anastomosis (IPAA) (Vasen, 2008). Genetic screening and endoscopy in concert with prophylactic surgery significantly improved the overall survival of FAP patients. A pharmacological prophylactic approach to prevent these outcomes for this population of patients is obviously in great need.

However, less well appreciated is the second leading cause of death in FAP, duodenal adenocarcinoma. Nearly 90% of patients with FAP develop duodenal polyps, the precursor lesions of duodenal adenocarcinoma and 4.5% will develop duodenal adenocarcinoma in their lifetime (Wallace, 1998; Bulow, 2004). In contrast to the colon, prophylactic surgical resection of the ampulla and/or duodenum is accompanied by significant morbidity. Duodenal surgery is currently indicated for patients with severe duodenal polyposis or duodenal carcinoma. This patient population has a strong need for adjuvant therapies to surgery to prevent or reduce the polyp formation and carcinogenesis in the gastrointestinal tract.

3. WNT Signaling Pathway

WNTs comprise a family of 19 secreted glycoproteins which function in diverse biological processes such as cell proliferation, survival and segment polarity during development (Anastas, 2013). WNTs signal via transmembrane receptors included in 10 member of the frizzled (FZD) family of G-protein coupled receptors and receptor tyrosine kinases. The first WNT gene was identified in cancer arising in mouse models of mammary cancer and in mouse and human colon cancer. WNTs promote stabilization of a transcription factor called β-catenin (also known as CTNNB1). WNTs control both the canonical β-catenin-dependent and non-canonical β-catenin-independent pathways. Studies point to a vital role for hyper-activated WNT-β-catenin signaling in colorectal cancer (Korinek, 1997; Morin, 1997). Inherited inactivating mutations of the adenomatous polyposis coli (APC) gene, the product of which is a negative controller of β-catenin stability, are found in patients with FAP. Polyps of FAP patients progress to colorectal carcinomas upon inactivation of the tumor suppressor p53 and activating mutations of KRAS. Both APC and CTNNB1 are commonly mutated in colorectal cancers of non-FAP patients.

The high prevalence of WNT pathway mutations in many types of cancer is evidence for the importance of the WNT-β-catenin pathway in carcinogenesis. Mutations in other members of the WNT signal pathway implicated in carcinogenesis include: TCF7L2 (transcription factor 7-like), CTNNB1, WTX (Wilms tumor gene on the X chromosome), and AXIN (See Table 1 of Anastas, 2013).

The risk for developing intestinal polyps or intestinal cancer may be determined by genetic analysis. The treatment or prevention of the disease may be instituted before or after any related surgical intervention such as polypectomy or any form of a full or partial colectomy or colon resection. Dosing regimens may include multiple doses per day, one dose per day, or regular doses one or more days apart.

In some aspects, colon-targeted, rapamycin-loaded microspheres can be used to treat or prevent some intestinal cancers, particularly colorectal cancer.

B. Vascular Cognitive Impairment

Vascular cognitive impairment is a cognitive impairment that results from underlying vascular pathology. Current approaches to treating and preventing vascular cognitive impairment focus on controlling risk factors for the vascular pathologies that underlie vascular cognitive impairment, such as high blood pressure, high cholesterol, high blood sugar or diabetes, or an autoimmune or inflammatory disease. While others have proposed treatments for some types of dementia, there is no known cure for vascular cognitive impairment, and no drug has been approved by the FDA for the treatment of vascular cognitive impairment. Thus, there is a need for methods and compositions that can treat and prevent vascular cognitive impairment.

The inventors and/or their collaborators have discovered an effective treatment for vascular cognitive impairment comprising rapamycin, an analog of rapamycin, or another inhibitor of mTOR. Alzheimer's disease (AD) in mice was found to exhibit underlying vascular pathology, which was improved by enteric-coated rapamycin treatment. The rapamycin treatment also improved the cognitive defects (e.g., learning and memory) that are characteristic of AD mice. Thus, rapamycin and other inhibitors of TOR (e.g., rapamycin analogs) can be used to treat or prevent vascular cognitive impairment.

The term "vascular cognitive impairment" refers to various defects caused by an underlying vascular pathology, disease, disorder, or condition that affects the brain. For example, strokes, conditions that damage or block blood vessels, or disorders such as hypertension or small vessel disease may cause vascular cognitive impairment. As used herein, the term "vascular cognitive impairment" includes mild defects, such as the milder cognitive symptoms that may occur in the earliest stages in the development of dementia, as well as the more severe cognitive symptoms that characterize later stages in the development of dementia.

The various defects that may manifest as vascular cognitive impairment include mental and emotional symptoms (slowed thinking, memory problems, general forgetfulness, unusual mood changes such as depression or irritability, hallucinations, delusions, confusion, personality changes, loss of social skills, and other cognitive defects); physical symptoms (dizziness, leg or arm weakness, tremors, moving with rapid/shuffling steps, balance problems, loss of bladder or bowel control); or behavioral symptoms (slurred speech, language problems such as difficulty finding the right words for things, getting lost in familiar surroundings, laughing or crying inappropriately, difficulty planning, organizing, or following instructions, difficulty doing things that used to come easily, reduced ability to function in daily life).

C. FCGS, AIHA, Lichen Planus, Lupus & Other Autoimmune Disorders

When orally administered daily, or at other regular frequencies (such as three times per week), in correspondingly effective doses, pharmaceutical preparations prepared according to the foregoing descriptions, and their equivalents, are thought to be effective for preventing and treating various autoimmune maladies in humans, canines, felines and other animals, and for delaying or reducing the progression of those maladies and their sequelae. For example, such oral administration in a canine subject enables prevention or treatment of canine hemolytic anemia and other autoimmune hemolytic anemias (AIHA), and such oral administration in humans or other animals enables prevention and treatment of lichen planus and lupus.

As another example, when orally administered daily or three times per week, or at other regular frequencies, in correspondingly effective doses, pharmaceutical preparations prepared according to the foregoing descriptions, and their equivalents, are effective for preventing and treating and reducing the progression of various gingival diseases. Preferably, preparations according to the preferred embodiments are administered at a regular frequency, preferably in periods in excess of one year on a daily or three times per week regiment. Note that dosing may occur more frequently or less frequently. Particularly identified gingival diseases include gingivitis stomatitis (a/k/a GingivoStomatitis), which includes diseases known as Lymphocytic or Plasmacytic GingivoStomatitis.

Figure 5:
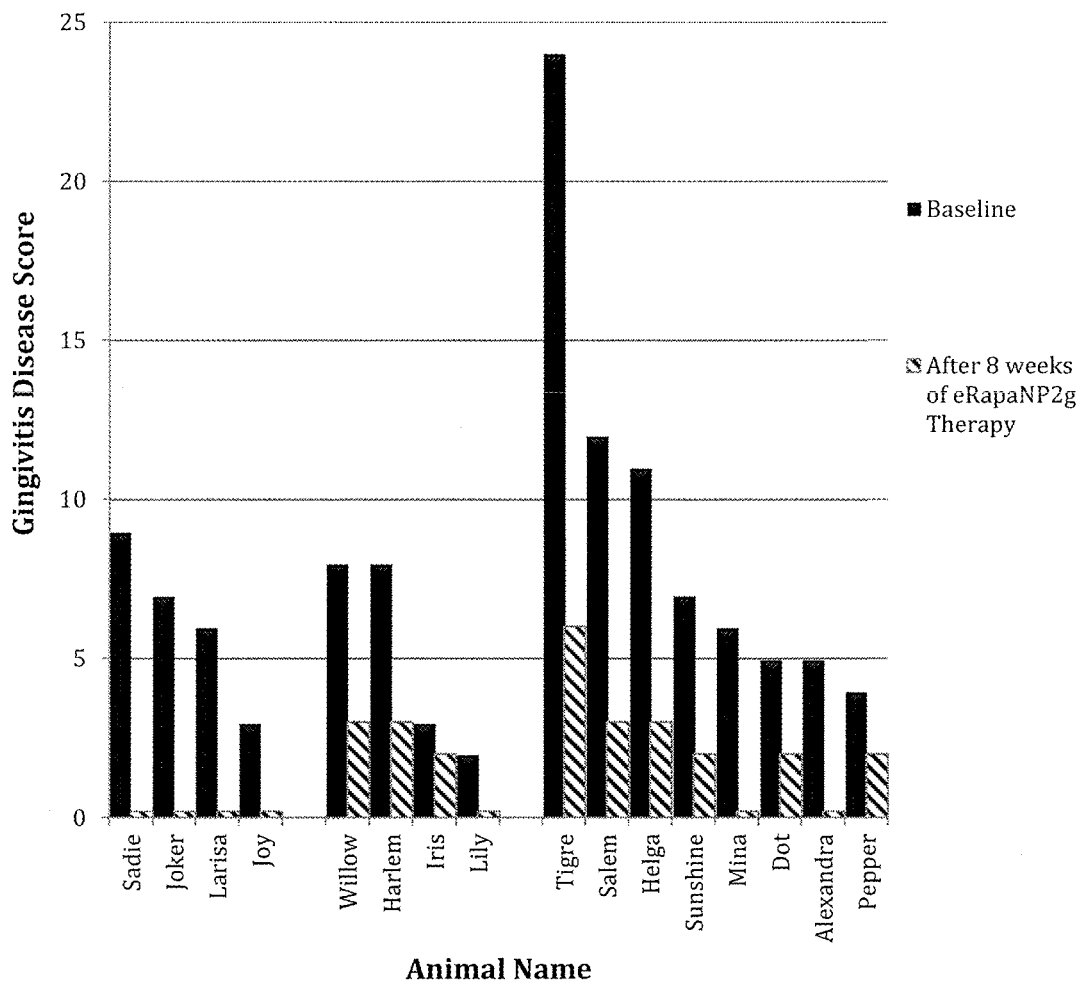
FIG. 5 presents summary data to illustrate how extended regular use of microencapsulated rapamycin nanoparticles was effective at reducing FCGS disease scores in 100% of sixteen feline subjects.

For instance, positive efficacy was observed in felines with chronic gingiva-stomatitis, when microencapsulated rapamycin nanoparticle preparations according to the present invention were administered three times a week orally, in capsules containing doses at 200, 400 and 600 micrograms/kilogram, variously for two, four, six and eight week durations. Particularly, in controlled studies following a protocol that confirmed the initial presence of medium to severe Feline Chronic Gingivostomatitis (FCGS), an autoimmune gingival disease, microencapsulated nanoparticle preparations produced according to the process illustrated in FIGS. 1-4B not only stopped progression of FOGS in all subjects tested, but also significantly reduced the severity of FOGS in most if not all of the tested subjects. More particularly, as illustrated in FIG. 5, a protocol of treating medium to severe FOGS with microencapsulated nanoparticle preparations produced according to the process illustrated in FIGS. 1-4B three times a week over 8 consecutive weeks showed reduced severity of FOGS in all sixteen of the feline subjects that participated in the study.

Particularly beneficial results are also appreciable through regular multi-week oral administration in the prevention and treatment of canine hemolytic anemia as well as gingival diseases. "Regular" oral administration may include oral administration of capsules, tablets or other oral dosing forms of microencapsulated rapamycin nanoparticles (or their equivalents) at least twice weekly, and preferably at least three times weekly, while alternative treatment protocols may be achieved through multiple dosings per day as well.

In any particular treatment protocol, it should be appreciated that dosing may vary based on particular needs and preferred treatment protocols according to preference, and depending on weight of the particular subject. Those of ordinary skill would understand that greater dose amount ranges would be tolerable and suitable when administered less often than once per day, and lesser ranges would be tolerable when administered more often than once per day.

Whereas prior art uses of rapamycin may have involved recommended daily dosings of roughly 13 micrograms per kilogram in human subjects, oncology protocols according to preferred embodiments of the present invention use higher dosings than the prior art, preferably in a range of more than 50 micrograms and up to (or even exceeding) 200 micrograms per kilogram for daily administration, or the equivalent for other frequencies of administration. Other conditions addressed by oral administration protocols of the present invention include preventing and treating hemolytic anemia in canines, felines, humans, and other animals, whether through the preferred preparations of rapamycin (or the equivalent) or through combination therapies with stem cell therapy and/or other active pharmaceutical or nutraceutical treatment protocols.

In contrast to oncology-related dosings, preferred protocols for oral administration of the preparations taught herein when used for prevention and treatment of targeted neurological conditions, and reducing the progression thereof, use lower dosings than the prior art. Such lower dosings are preferably about 5 micrograms of bioavailable rapamycin (or the equivalent) per daily oral dose, and such dosings otherwise more generally fall in the preferred range of between 1 and 7 micrograms per kilogram for once-daily administration, or the equivalent for other frequencies of administration.

Although various indications are targeted in alternative embodiments, preferred embodiments of oral administration protocols according to the present invention are, more stable, more bioavailable and efficacious, and finds better biodistribution, for treatment and prevention and reducing the progression of genetically-predisposed disorders and age-related disorders, with surprising benefits especially in the fields of the prevention and treatment of hemolytic anemia in canines and gingivitis in felines and is thought to have analogous benefits in humans and other animals.

EXAMPLES

A. Intestinal Cancer and Familial Adenomatous Polyposis (FAP)

Various studies related to FAP and colon cancer with administration of encapsulated rapamycin have shown increased life span in mouse models for FAP, reduced polyp counts in such mouse models, prevention of polyp development and progression, and increased activity levels in mouse models treated with encapsulated rapamycin.

One particular study completed by Applicants' collaborators showed increased life span in a mouse model referred to as Apc$^{Min/+}$, a model which tends to develop multiple intestinal neoplasms early in life. As a consequence, this mouse model has a short life span, typically about 180 days.

Mice in the study received either control chow containing no enteric-coated rapamycin or one of two doses of enteric-coated rapamycin, 14 ppm encapsulated rapamycin (2.24 mg/kg/day) or 42 ppm encapsulated rapamycin (6.72 mg/kg/day).

Results of this study showed that rapamycin-treated mice had an increased life span, these mice surviving between 570 and 1,093 days, the longer life spans correlating with the higher dose of enteric-coated rapamycin administered. In contrast, none of the control mice survived more than 181 days. Results also indicated that the rapamycin-treated mice had a reduced intestinal polyp count or even no intestinal polyps present as determined by necropsy performed at the conclusion of the study. Moreover, the rapamycin-treated mice exhibited increased activity levels as compared to the mice that were not treated with rapamycin. It was also observed that the higher dose of enteric-coated rapamycin was more effective at maintaining normal hematocrits as compared to wild-type mice, even at an age when 5% of such wild-type mice were reported to die of natural causes. Results have also shown positive effects on the intestines of mice treated with encapsulated rapamycin, the doses being the same as indicated above, namely a control group not receiving rapamycin and two different dosing groups being 14 ppm encapsulated rapamycin and 42 ppm encapsulated rapamycin. C57BL/6 mice were used in this particular study. Specifically, other study results were observed wherein the proximal and distal portions of the small intestine of encapsulated rapamycin-treated mice were assayed with the results indicating mTORC1 inhibition in both the proximal and distal areas of the small intestine, demonstrated by the inhibition of ribosomal protein S6 (rpS6) Ser 240/244 phosphorylation. Furthermore, depression of rpS6 phosphorylation as observed indicated a decrease in ribosome biogenesis which, in turn, would result in inhibition of cell growth required for polyp formation.

Higher blood concentrations of rapamycin were also observed with an increase noted in the distal intestine as compared with the proximal intestine. More particularly, blood levels in mice receiving the higher dose show a more than 4-fold increase in average blood levels of rapamycin as compared to the lower administered dose. These concentrations were observed to be higher than the therapeutic range for recipients of organ transplants. The greater concentration of rapamycin observed in the distal intestine in comparison to that found in the proximal intestine is thought to correlate with the pH gradient through the intestine as well as an increase in drug release from the enteric coating based on the pH-dependent dissolution of that enteric coating.

Also assessed were the effects of enteric-coated rapamycin on the colons of C57BL/6 mice since FAP patients are known to develop colonic neoplasia. Results indicated that treatment with enteric-coated rapamycin produced a significant reduction in Ser240/244 phosphorylation in the colon which is consistent with release of rapamycin in the colon.

These studies indicate that enteric-coated rapamycin targeting the intestine of the mouse models works to prevent polyp development and progression, one effect of which is an extension of life span. Such results suggest that targeting encapsulated rapamycin to the colon may be highly efficacious in treating and preventing colorectal cancer, FAP, and other similar or related intestinal diseases.

B. Vascular Cognitive Impairment

Other studies have been conducted which indicate an effective role for encapsulated rapamycin as taught herein in treating and preventing cognitive disorders including, but not limited to, vascular cognitive impairment and Alzheimer's disease (AD).

One particular study was conducted to determine the effects, if any, of treatment with rapamycin on deficits in transgenic PDAPP mice, a model for Alzheimer's disease. The mice were treated with rapamycin over a total of 16 weeks. Both the control group and the mice treated with rapamycin exhibited AD symptoms prior to initiation of the study protocol.

Spatial training in a Morris water maze was utilized as a means to measure the effects of rapamycin treatment as compared to control. Control mice exhibited significant deficits during training, with performance worsening as the training progressed. In contrast, learning deficits in rapamycin-treated mice were improved. Moreover, the rapamycin-treated mice showed an improved performance as the training proceeded. Memory was also shown to be markedly better in the rapamycin-treated mice in contrast to control. Also observed were the effects of chronic treatment with rapamycin on the hemodynamic function in brains of AD mice. Vascular abnormalities in control mice were suggested by a measurably lower global cerebral blood flow (CBF). However, in rapamycin-treated mice, CBF was not distinguishable from non-transgenic groups. More specifically, CBF in the hippocampus was reduced in control mice, but treatment with rapamycin restored these CBF levels such that they were comparable with non-transgenic groups. The significance of this would be readily appreciated by those of skill in the art since synaptic dysfunction is known to occur in the hippocampus in the early stages of AD. Relatedly, it was also observed that the control mice exhibited reduced cerebral vessel density which was abrogated by chronic rapamycin treatment.

It was also observed that treatment with encapsulated rapamycin to maintain vascular integrity led to a decrease in Aβ deposition in brain vessels, a reduction in Aβ plaque, and fewer microhemorrhages in AD brains. Overall, the results observed in this study suggest treatment with encapsulated rapamycin can improve cognitive function in AD mice.

C. Feline Chronic Gingivostomatitis (FCGS)

Positive efficacy was observed in felines with chronic gingiva-stomatitis, when microencapsulated rapamycin nanoparticle preparations according to the present invention were administered three times a week orally, in capsules containing doses at 200, 400 and 600 micrograms/kilogram, variously for two, four, six and eight week durations. Particularly, in controlled studies following a protocol that confirmed the initial presence of medium to severe Feline Chronic Gingivostomatitis (FOGS), an autoimmune gingival disease, microencapsulated nanoparticle preparations produced according to the process illustrated in FIGS. 1-4 not only stopped progression of FOGS in all subjects tested, but also significantly reduced the severity of FOGS in most if not all of the tested subjects. More particularly, as illustrated in FIG. 5, a protocol of treating medium to severe FCGS with microencapsulated nanoparticle preparations produced according to the process illustrated in FIGS. 1-4 three times a week over eight consecutive weeks showed reduced severity of FOGS in all 16 of the feline subjects that participated in the study.

Many of the studies described above provide evidence for an effective role for enteric-coated rapamycin as well as microencapsulated rapamycin nanoparticles as taught herein.

Alternative Embodiments with Other Rapamycins

Although many aspects of the present invention relate directly to rapamycin itself, possible broader aspects of the invention relate also to analogs and derivatives of rapamycin, and to producing a more stable and effective oral preparation for delivering an agent to bind, interact with or otherwise regulate activity of the mTOR pathway.

Accordingly, as alternatives that benefit from many but not necessarily all of the teachings of the present invention, any of the particular embodiments described above may be modified by substituting one or more other rapamycins in place of (or in addition to) rapamycin. For corresponding purposes of these descriptions, rapalogs and all mTOR pathway inhibitors should be considered as "rapamycins" (i.e., the plural of rapamycin). Also, in this context and wherever else a context relates to any of the rapamycins rather than just rapamycin, any related references to "encapsulated rapamycin" should be read as teaching not only about discrete particles that include rapamycin, but also about discrete particles that include any one or more rapamycins.

Administration in Combination with Other Therapies

It should be understood that the foregoing disclosure emphasizes certain specific embodiments of the invention. Alternative embodiments may involve administration of rapamycin in combination with other therapies. Such therapies include but are not limited to dental scaling; long term use of antibacterial dental hygiene products; professional scaling and long-term tooth brushing with 0.2% chlorohexidine; corticosteroids, gold salts; antibiotics; chlorhexidine gluconate gel; radical dental extraction techniques of premolars, molars or other teeth; radiation therapy; cryotherapy; antibiotics with activity against gram-negative and anaerobic organisms (including amoxicillin-clavulanic acid combination, enrofloxacin, lincomycin, clindamycin, spiramycin, metronidazole, and tetracyclines); corticosteroids; subgingival injection of up 10 milligrams triamcinolone; long-term prednisolone, methylprednisolone, or triamcinolone; methylprednisolone; sodium aurothiomalate; aurothioglucose; azathioprine; cyclophosphamide; chlorambucil; immunostimulatory; PIND-ORF; megestrol acetate; lactoferrin; sodium salicylate; meloxicam; interferon; thalidomide; anti-viral agents; AZT; PMEA; soft-tissue lasers; multivitamin; antioxidant supplementation; and chemical cautery.

General Alternatives

It should be understood that the foregoing disclosure emphasizes certain specific embodiments of the invention and that all substitutions, modifications or alternatives equivalent thereto should be presumed to fall within the spirit and scope of the invention. While reference is made in many respects to incorporation of various rapamycin nanoparticle embodiments, it should also be recognized that the spirit and scope of the invention may not be limited to nanoparticles as such, nor to the other particular compounds or the like referenced herein.

In all respects, it should also be understood that the drawings and detailed description herein are to be regarded in an illustrative rather than a restrictive manner, and are not intended to limit the invention to the particular forms and examples disclosed. Rather, the invention includes all embodiments and methods within the scope and spirit of the invention as claimed, as the claims may be amended, replaced or otherwise modified during the course of related prosecution. Any current, amended, or added claims should be interpreted to embrace all further modifications, changes, rearrangements, substitutions, alternatives, design choices, and embodiments that may be evident to those of skill in the art, whether now known or later discovered. In any case, all substantially equivalent systems, articles, and methods should be considered within the scope of the invention and, absent express indication otherwise, all structural or functional equivalents are anticipated to remain within the spirit and scope of the present inventive system and method.

It is also specifically contemplated that any of the particular encapsulated rapamycin embodiments described herein may be provided in daily oral doses (once or twice daily) for any of the medical or veterinary applications referenced throughout this specification or that may be referenced in US Patent Application 2012/0064143 and any other publications describing possible uses for encapsulated rapamycin. It should also be understood that the dosing regimens described herein with regard to specific indications may also be used with any or all of the other indications discussed. Dosing regimen would include both the concentration of rapamycin administered as well as the frequency of administration.

Alternative embodiments of the present invention include administering rapamycin locally to the oral cavity and at least one polymer, such that said system is attached to a surface in the oral cavity and remains attached thereto for at least 1 hour. Administration may also include a sustained release and a liquid precursor varnish composition to this system. This process is discussed in detail in Friedman et al., (US 2013/0018069), which is incorporated by reference.

For other alternatives, it should be understood that any limitation discussed with respect to one embodiment of the invention may apply to any other embodiment of the invention. Moreover, any composition of the invention may be used in any method of the invention, and any method of the invention may be used to produce or to utilize any composition of the invention. Any embodiment of the present invention may consist of or consist essentially of—rather than comprise/include/contain/have—the described features and/or steps.

Accordingly and otherwise, many other alternatives will be evident to those of skill in the art. Rather than being limited by the embodiment descriptions as set forth above, the invention itself should ultimately be contemplated based on any claims that may be appended hereto or added in the course of prosecuting this patent application or other patent applications that claim direct or indirect priority to this patent application. All descriptive materials referenced herein are incorporated by reference in their entirety, for all purposes. These descriptive materials include: Feline Gingivostomatitis, Ross Harley PhD; Feline Chronic Gingivitis Stomatitis, Dentalvets 2013, at the following web address: http://www.dentalvets.co.uk/files/Docs/Common%20Case%20Types/FCGS/FCGS_May2 013.pdf; *The Disease Formerly Known as Lymphocytic/Plasmacytic Gingivo-stomatitis*, Fraser A. Hale, www.toothvet.com (December 2010).

We claim:

1. A microparticle pharmaceutical preparation, comprising:
 a) an enteric coating comprising a solid excipient matrix, said solid excipient matrix comprising a polymer composition that remains intact when exposed to acidic conditions of the alimentary canal of an animal and that disintegrates in near-neutral to basic conditions of targeted portions of said alimentary canal, said polymer composition comprising a copolymer of methacrylic acid and methyl methacrylate;
 b) nanoparticles dispersed within said solid excipient matrix, said nanoparticles comprising:
  1) a micelle-inducing compound, said micelle-inducing compound comprising sodium cholate;
  2) a pharmaceutically active core comprising rapamycin or an analog of rapamycin;
 c) said micelle-inducing compound naturally inducing formation of micelles, said micelles having properties that promote stability of said rapamycin or said analog of rapamycin when said nanoparticles are dispersed within said solid excipient matrix.

2. The pharmaceutical preparation of claim 1, wherein said nanoparticles are sized in the range between about 1 nanometer to about 1 micron.

3. The pharmaceutical preparation of claim 1, wherein said copolymer further comprises methacrylic acid and methyl methacrylate at a ratio of 1:2.

4. The pharmaceutical preparation of claim 1, wherein said copolymer further comprises methacrylic acid and methyl methacrylate at a ratio of 1:1.

5. The pharmaceutical preparation of claim 1, wherein said polymer composition has a dissolution pH of about 7.

6. The pharmaceutical preparation of claim 1, wherein said analog of rapamycin is selected from the group consisting of everolimus, temserolimus, tacrolimus, prerapamycin, zotarolimus, ridaforolimus, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, and 42-O-(2-hydroxy)ethyl rapamycin, rapamycin oximes, rapamycin aminoesters, rapamycin dialdehydes, rapamycin 29-enols, O-alkylated rapamycin derivatives, water soluble rapamycin esters, alkylated rapamycin derivatives, rapamycin amidino carbamates, biotin esters of rapamycin, carbamates of rapamycin, rapamycin hydroxyesters, rapamycin 42-sulfonates, 42-(N-carbalkoxy)sulfamates, rapamycin oxepane isomers, imidazolidyl rapamycin derivatives, rapamycin alkoxyesters, rapamycin pyrazoles, acyl derivatives of rapamycin, rapamycin amide esters, rapamycin fluorinated esters, rapamycin acetals, oxorapamycins, and rapamycin silyl ethers.

* * * * *